(12) United States Patent
Spearman et al.

(10) Patent No.: US 11,752,020 B2
(45) Date of Patent: Sep. 12, 2023

(54) TOOL FOR PLACEMENT OF DEGRADABLE OSTIAL STENT

(71) Applicants: Michael J. Spearman, The Midlands, TX (US); John H. Burban, Lake Elmo, MN (US); Peter J. Catalano, Newton, MA (US); Brian M. Spearman, The Woodlands, TX (US); Keith A. Roberts, Dellwood, MN (US); John W. Shanahan, White Bear Lake, MN (US)

(72) Inventors: Michael J. Spearman, The Midlands, TX (US); John H. Burban, Lake Elmo, MN (US); Peter J. Catalano, Newton, MA (US); Brian M. Spearman, The Woodlands, TX (US); Keith A. Roberts, Dellwood, MN (US); John W. Shanahan, White Bear Lake, MN (US)

(*) Notice: Subject to any disclaimer, the term of this patent is extended or adjusted under 35 U.S.C. 154(b) by 0 days.

(21) Appl. No.: 16/903,815

(22) Filed: Jun. 17, 2020

(65) Prior Publication Data

US 2020/0397605 A1 Dec. 24, 2020

Related U.S. Application Data

(60) Provisional application No. 62/863,309, filed on Jun. 19, 2019.

(51) Int. Cl.
*A61F 2/82* (2013.01)
*A61F 2/962* (2013.01)

(52) U.S. Cl.
CPC ............... *A61F 2/962* (2013.01); *A61F 2/82* (2013.01); *A61F 2002/821* (2013.01);
(Continued)

(58) Field of Classification Search
CPC .... A61F 2210/0061; A61F 2/962; A61F 2/82; A61F 2002/821; A61F 2010/0004;
(Continued)

(56) References Cited

U.S. PATENT DOCUMENTS

| 5,047,053 A | * | 9/1991 | Jahn | A61F 11/002 |
| | | | | 623/10 |
| 5,246,455 A | * | 9/1993 | Shikani | A61F 2/18 |
| | | | | 623/10 |

(Continued)

OTHER PUBLICATIONS

Medtronic Delivery Systems Catalog, Attain Deflectable Catheter, <https://www.medtronic.com/us-en/healthcare-professionals/products/cardiac-rhythm/crt-systems/delivery-systems.html> Accessed Jun. 10, 2021. (FDA cleared 2003) (Year: 2003).*

(Continued)

*Primary Examiner* — Keri J Nelson
*Assistant Examiner* — Aren Patel
(74) *Attorney, Agent, or Firm* — Mark A. Litman & Associates, P.A.

(57) ABSTRACT

A hand-held device is used to deliver and hydrate a temporary polymeric implant having a length, an outer surface and a cross-section, with a disruptable cover over the implant. A lumen may pass through the entire length, the lumen having a surface forming an equivalent diameter in the polymeric stent. The temporary polymeric implant includes a first aqueous-swellable, biocompatible and biodegradable composition (e.g., polymer) having a thickness. The aqueous-swellable and biodegradable polymer retaining structural integrity for at least 1 hours up to thirty days when swollen and kept moist by a moist aqueous environment. Barrier layers of biodegradable polymer(s) may be used to prevent migration of liquids into the lumen.

17 Claims, 10 Drawing Sheets

(52) U.S. Cl.
CPC .............. *A61F 2210/0004* (2013.01); *A61F 2210/0061* (2013.01); *A61F 2210/0076* (2013.01); *A61F 2230/0069* (2013.01)

(58) Field of Classification Search
CPC ...... A61F 2010/0061; A61F 2010/0076; A61F 2230/0069
See application file for complete search history.

(56) References Cited

U.S. PATENT DOCUMENTS

| | | | | |
|---|---|---|---|---|
| 5,336,163 | A * | 8/1994 | DeMane | A61F 13/36 128/206.11 |
| 5,601,594 | A * | 2/1997 | Best | A61F 5/08 606/196 |
| 5,782,848 | A * | 7/1998 | Lennox | A61B 1/12 600/569 |
| 5,807,327 | A * | 9/1998 | Green | A61F 2/958 623/1.11 |
| 6,030,397 | A * | 2/2000 | Monetti | A61B 17/320758 606/159 |
| 6,042,574 | A * | 3/2000 | O'Halloran | A61F 11/002 128/864 |
| 6,606,995 | B1 * | 8/2003 | Sadek | A61F 5/08 128/207.14 |
| 7,691,094 | B2 * | 4/2010 | Eaton | A61K 9/0024 604/506 |
| 8,114,113 | B2 * | 2/2012 | Becker | A61M 3/0295 606/196 |
| 8,277,478 | B2 * | 10/2012 | Drontle | A61M 25/10 606/196 |
| 8,313,762 | B2 * | 11/2012 | Oliver | A61L 24/0042 424/426 |
| 8,317,816 | B2 * | 11/2012 | Becker | A61M 25/1002 606/196 |
| 8,764,729 | B2 * | 7/2014 | Muni | A61B 17/24 604/514 |
| 8,827,953 | B2 * | 9/2014 | Rocha-Singh | A61M 25/1011 604/101.02 |
| 8,974,486 | B2 * | 3/2015 | Kotler | A61M 16/0666 606/199 |
| 9,039,657 | B2 * | 5/2015 | Makower | G03G 5/0614 604/96.01 |
| 9,351,750 | B2 * | 5/2016 | Muni | A61F 11/004 |
| 9,486,614 | B2 * | 11/2016 | Drontle | A61M 29/02 |
| 9,568,681 | B2 * | 2/2017 | Roussel | G02B 6/36 |
| 9,579,448 | B2 * | 2/2017 | Chow | A61M 25/1018 |
| 2001/0025155 | A1 * | 9/2001 | Yoon | A61M 25/10 604/1 |
| 2002/0099431 | A1 * | 7/2002 | Armstrong | A61F 2/97 623/1.11 |
| 2003/0028237 | A1 * | 2/2003 | Sullivan | A61F 2/07 623/1.11 |
| 2003/0040733 | A1 * | 2/2003 | Cragg | A61B 17/12177 604/508 |
| 2003/0045923 | A1 * | 3/2003 | Bashiri | A61F 2/91 623/1.12 |
| 2003/0187381 | A1 * | 10/2003 | Greenawalt | A61L 31/042 604/11 |
| 2004/0254625 | A1 * | 12/2004 | Stephens | A61B 17/12136 623/1.1 |
| 2005/0191331 | A1 * | 9/2005 | Hunter | A61B 17/1219 424/423 |
| 2006/0063973 | A1 * | 3/2006 | Makower | A61B 1/018 600/114 |
| 2006/0095066 | A1 * | 5/2006 | Chang | A61M 25/10 606/199 |
| 2006/0210605 | A1 * | 9/2006 | Chang | A61B 17/24 424/434 |
| 2007/0038226 | A1 * | 2/2007 | Galdonik | A61B 17/22 606/114 |
| 2007/0043381 | A1 * | 2/2007 | Furst | A61F 2/966 623/1.11 |
| 2008/0275536 | A1 * | 11/2008 | Zarins | A61F 2/07 623/1.11 |
| 2009/0299393 | A1 * | 12/2009 | Martin | A61B 17/221 606/159 |
| 2010/0106178 | A1 * | 4/2010 | Obermiller | A61B 17/0057 606/194 |
| 2011/0160740 | A1 * | 6/2011 | Makower | A61M 25/1011 606/115 |
| 2012/0302950 | A1 * | 11/2012 | Landsman | A61M 25/0043 604/95.05 |
| 2014/0276408 | A1 * | 9/2014 | Abbate | A61M 29/00 604/106 |
| 2015/0238739 | A1 * | 8/2015 | Cully | A61B 17/00 606/194 |
| 2015/0306282 | A1 * | 10/2015 | Scanlon | A61L 31/14 623/1.11 |
| 2016/0024285 | A1 * | 1/2016 | Delli-Santi | A61L 31/145 106/122 |
| 2016/0030047 | A1 * | 2/2016 | Allen | A61B 17/1214 606/200 |
| 2016/0184564 | A1 * | 6/2016 | Spearman | A61M 31/00 604/516 |
| 2018/0071118 | A1 * | 3/2018 | Spearman | A61F 2/82 |
| 2019/0192318 | A1 * | 6/2019 | Spearman | A61L 31/148 |
| 2019/0350731 | A1 * | 11/2019 | Liu | A61F 2/91 |
| 2020/0397605 | A1 * | 12/2020 | Spearman | A61F 2/962 |

OTHER PUBLICATIONS

Medtronic 510(k) Summary of Substantial Equivalence from the FDA, pp. 1-6. <https://www.accessdata.fda.gov/cdrh_docs/pdf3/K031211.pdf>. Accessed Jun. 10, 2021. (date signed 2003) (Year: 2003).*

* cited by examiner

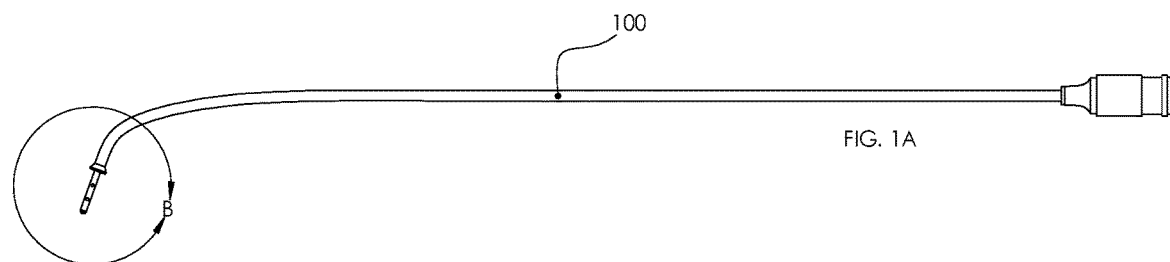
FIG. 1A
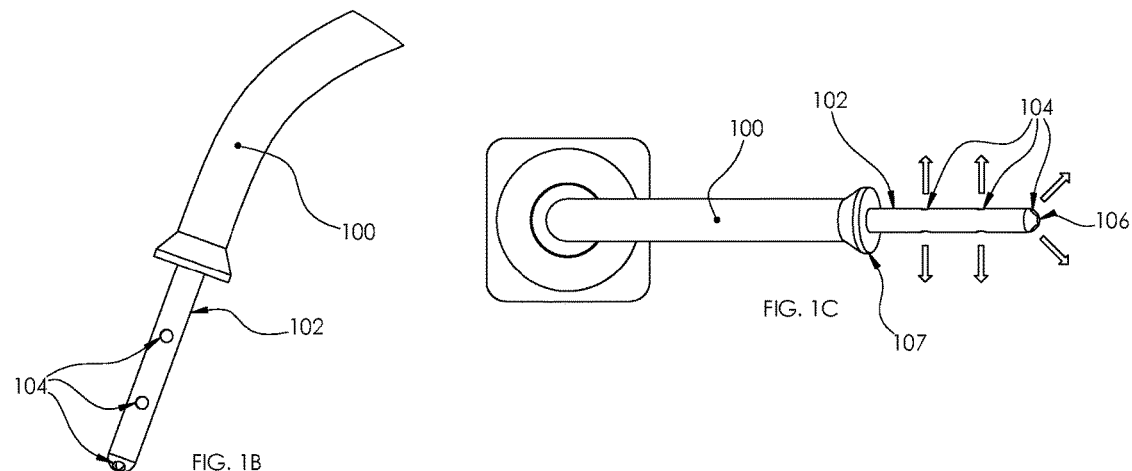
FIG. 1B
FIG. 1C

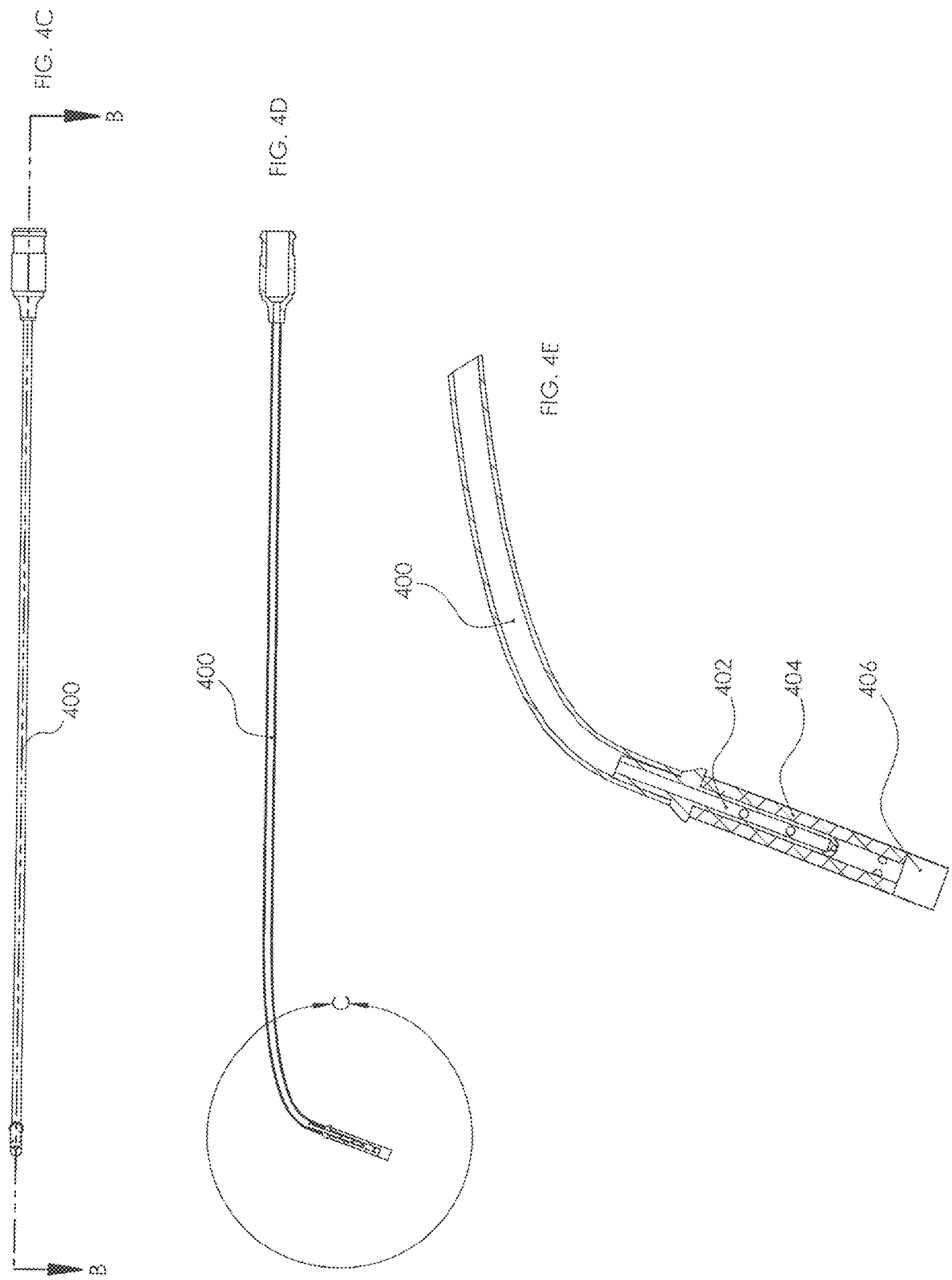

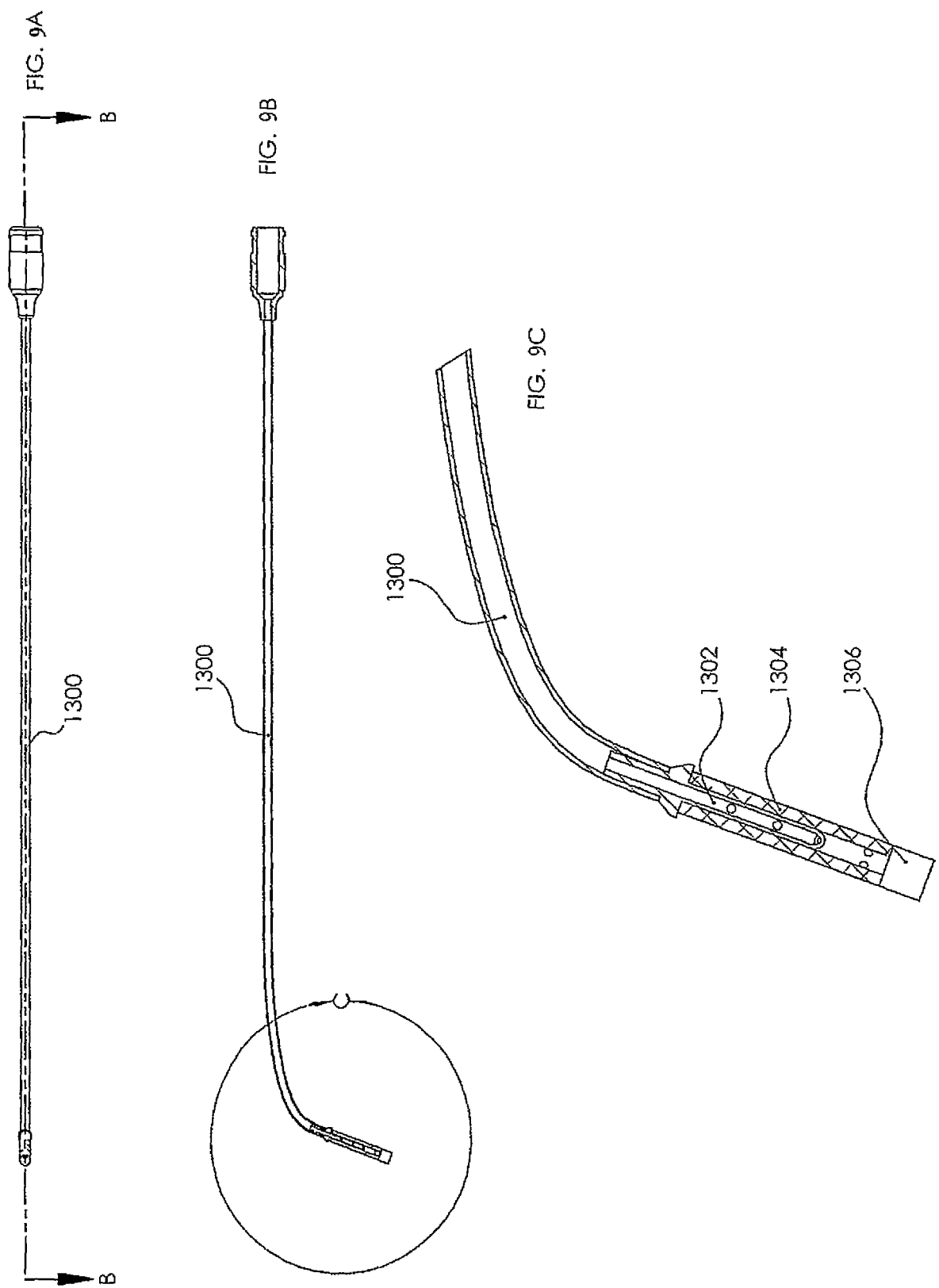

TOOL FOR PLACEMENT OF DEGRADABLE OSTIAL STENT

RELATED APPLICATION DATA

The present application claims priority under 35 U.S.C. 120 as a continuation-in-part of Provisional U.S. Patent Application Ser. No. 62/733,815, filed 20 Sep. 2018, titled TOOL FOR PLACEMENT OF DEGRADEABLE OSTIAL STENT, which in turn claims priority under 35 USC 120 from U.S. patent application Ser. No. 15/266,659, DEGRADEABLE OSTIAL STENT, filed 16 Sep. 2016, now U.S. Pat. No. 10,265,201.

BACKGROUND OF THE INVENTION

1. Field of the Invention

The present invention relates to the field of medical treatments in body cavities or passages, and particularly non-arterial stent placement, and especially ostial, duct, tube (and the like) stent, sponge, wicking or delivery (implantable) implement placement, and more particularly to the implement to be placed and tools and procedures for placement and hydration or activation of implantable implement in a patient.

BACKGROUND OF THE ART

There are a significant number of medical conditions and their attendant treatments that require maintaining fluid flow and/or continuity within specific regions of the human anatomy. The most common method of fluid flow maintenance is through the use of stents. Stents have been used in many different positions, including vascular (arterial and venal) stents, organ duct stents, lachrymal stents, ear drum tubes, ostial stents and the like. Although each type of stent is a variant in structure and composition of a tube-like element, the dimensions, compositions, and properties of the stents must differ from each environment to properly function. For example, the metal, composition or polymeric stents used in vascular stenting (where a more permanent implantation is desired) would be inappropriate for ear drum stenting or lachrymal stents, which tend to be more temporary insertions.

Many different structures and compositions are known in this field of technology, and some of them are described in the prior art noted below.

US Patent Publication No. 20160024285 (Delli-Santi) describes a resilient foam and methods of making the foam. The resilient foam includes a derivatized polyanionic polysaccharide and has an open-cell structure. When the resilient foam is contacted with water, the foam forms a thixotropic hydrogel. A wide range of polyanionic polysaccharides are suitable for the invention. Non-limiting examples of polyanionic polysaccharides include modified starch and cellulose. Non-limiting examples of derivatized polyanionic polysaccharides include carboxymethyl cellulose, cellulose ethyl sulfonate, carboxymethyl amylose, chondroitin-6-sulfate, chondroitin-4-sulfate, dermatan sulfate, alginate, heparin, heparin sulfate, or any combination thereof. In some embodiments, the derivatized polyanionic polysaccharide is dissolvable. The resilient foam can include 40 wt. % or more of derivatized polyanionic polysaccharide.

Bioresorbable gels and stents are also described in U.S. Pat. No. 8,313,762, and U.S. Patent Application Publication No. 2003/0187381.

U.S. Patent Publication 20150306282 (Scanlon) describes a high strength, bioresorbable wall thickness suitable for use in an endoprosthesis such as a stent that is produced by first forming a wall thickness by melt processing or solution processing one or more bioresorbable materials into a tubular shape; drawing the shape from shorter length to an optimum longer length and reducing the diameter from a larger diameter to a smaller diameter to orient the molecular chains of the material; fabricating a stent from the tube formed of the oriented material by cutting a strut pattern in its wall thickness; covering the stent's struts with at least one coating to delay degradation of the bioresorbable material; covering the stent's struts with one or more controlled release active ingredients to minimize the risk of restenosis or other side effects; crimping the stent onto a balloon catheter assembly; delivering the stent into an anatomical lumen via percutaneous methods to a treatment location; radially expanding the stent from a smaller size to a larger size at the treatment location wherein the stent temporarily supports the anatomical lumen; and removing the catheter from the lumen. Many categories of stents, including nasal stents are disclosed.

U.S. Pat. No. 8,974,486 (Kotler) provides methods and devices for maintaining nasal passages open after nasal surgery. The post-operative device includes a first tubular member with a first proximal end and a first distal end, and a second tubular member with a second proximal end and a second distal end, where the first proximal end is connected to the second proximal end with a bridging member. The method includes inserting the post-operative device into the nasal passages and before, during or after inserting the device into the nasal passages, adjusting the medical device to accommodate the nasal passages by manipulating a flexible member of the medical device.

The endoprosthesis of that invention includes applications selected from the group of: coronary vascular stent; a vascular stent; a peripheral vascular stent; a carotid stent; a cerebral stent; a cell transportation device; a cell growth platform; a device for supporting an anatomical lumen; a device for reinforcing an anatomical lumen; a device for delivering a drug or drugs to an anatomical lumen; a renal stent; a iliac stent; a superficial femoral artery stent; a urethral stent; a ureter stent; a urinary stent; a biliary stent; an implantable scaffold; a tracheal stent; a trachea stent; a large bronchi stent; a nasal stent; a gastrointestinal stent; an esophageal stent; a drug delivery stent; a drug delivery device; a self-expandable stent; a balloon-expandable stent; a coil stent; a helical spiral stent; a woven stent; an individual ring stent; a ratcheting stent; a modular stent; a bifurcated stent; a stent-graft; a graft; a birth control device; an intrauterine device (IUD); an anatomical lumen repair or splicing device; a device for local delivery of active ingredients to tubular shaped lumen or organs for treatment of cancer; a device for treatment of colon or rectal cancer; an implant; a patch; a mechanical support device; a reinforcement device; a repair device; an attachment device; an oncology treatment device; a device for treatment of cancer within or near an anatomical lumen; a device to assist in remodeling of diseased anatomical lumens; a tissue engineering application (bone, cartilage, blood vessels, bladder, skin, muscle, etc.); a bone fixation device; bone plates; a medical textile; a repair, a device for reconstruction, or replacement/repair of ligaments; a device for maxillofacial surgery; a device for repair, reconstruction, or replacement of rotator cuffs; a device for repair, reconstruction, replacement of hollow organ tissue; a screw; a plate; any implantable devices, patches, regenerative medicine; and a device for the treatment of cancer An ENT stent may be a choanal atresia stent composed of two long hollow tubes that are bridged by a flexible transverse tube. See, e.g., U.S. Pat. No. 6,606,995. The ENT stent may be an expandable nasal stent for postoperative nasal packing composed of a highly porous, pliable and absorbent foam material capable of expanding outwardly, which has a non-adherent surface. See, e.g., U.S. Pat. No. 5,336,163. The ENT stent may be a nasal stent composed of a deformable cylinder with a breathing passageway that has a smooth outer non-absorbent surface used for packing the nasal cavity following surgery. See, e.g., U.S. Pat. No. 5,601,594. The ENT stent may be a ventilation tube composed of a flexible, plastic, tubular vent with a rectangular flexible flange which is used for the nasal sinuses following endoscopic antrostomy. See, e.g., U.S. Pat. No. 5,246,455. The ENT stent may be a ventilating ear tube composed of a shaft and an extended tab which is used for equalizing the pressure between the middle ear and outer ear. See, e.g., U.S. Pat. No. 6,042,574. The ENT stent may be a middle ear vent tube composed of a non-compressible, tubular base and an eccentric flange. See, e.g., U.S. Pat. No. 5,047,053. ENT stents, which may be combined with the compounds according to the present disclosure, include commercially available products such as Genzyme Corporation (Ridgefield, N.J.) SEPRAGEL Sinus Stents, the MEROGEL Nasal Dressing and Sinus Stents from Medtronic Xomed Surgical Products, Inc. (Jacksonville, Fla.), the POLYFLEX Stent from Rusch (Germany), and the FREEMAN Frontal Sinus Stent from InHealth Technologies (Carpinteria, Calif.). Other exemplary products which may be combined with the compounds described include the RELIEVA Balloon Sinuplasty (Acclarent Inc., Menlo Park, Calif.) catheter-based devices made of flexible tubes with a balloon on the distal end. These devices are configured to track over the sinus guidewire to the blocked ostium, which is then gradually inflated to gently restructure the ostium and are intended for clearing blocked sinuses, restoring normal sinus drainage and function, and preserving normal anatomy and mucosal tissue. See, for example, US Patent Applications 2006/0210605; 2006/0063973; and 2006/0095066.

U.S. Patent Publication No. 20050191331 (Hunter) describes implants that are used in combination with an anti-scarring agent in order to inhibit scarring that may otherwise occur when the implant is placed within an animal. The agent may be any suitable anti-scarring agent, e.g., a cell cycle inhibitor, and may be used in conjunction with a second pharmaceutical agent, e.g., an antibiotic. Suitable implants include intravascular implants, a vascular graft or wrap implant, an implant for hemodialysis access, an implant that provides an anastomotic connection, ventricular assist implant, a prosthetic heart valve implant, an inferior vena cava filter implant, a peritoneal dialysis catheter implant, a central nervous system shunt, an intraocular lens, an implant for glaucoma drainage, a penile implant, a endotracheal tube, a tracheostomy tube, a gastrointestinal device, and a includes spinal implant.

All cited documents are incorporated herein by reference in their entirety.

Stents, and especially ostial stents having properties determined to be specific to that environment are desirable. The present technology enables low cost, fast self-securing, efficient ostial stents that resorb in the body under normal conditions, and thus mitigate the potential for adverse reactions derived from the location of a foreign body in the sinus cavities.

No tool is available that specifically is designed to work advanced types of nasal dressings. However, the prior art is rich with devices and tools for balloon sinuplasty and for placement of expandable drug eluting devices that degrade or are removed with time. There are significant numbers of manufacturers in balloon sinuplasty. These include Acclarent (U.S. Pat. Nos. 8,114,113; 8,317,816; 8,764,729; 8,858,586; 8,968,269; 9,039,657; 9,351,750; 9,579,448; 9,649,477) and Entellus (U.S. Pat. Nos. 8,277,478; 9,486,614; 8,986,340) and Medtronic. While this existing technology may have some superficially common appearance features with respect to the present inventive technology, since the present technology accesses the same anatomy of the patient, these existing systems all are used to enlarge the ostial opening by inflating a balloon.

The present invention does not have a balloon and does not perform the same function as the tools of the prior art. In fact, the present invention device is preferably used and placed after balloon sinuplasty to keep the hole patent (available in size for ostial stent insertion), and provide a benign environment for healing. The present technology can also be used to deliver beneficial substances at a controlled rate to the body—i.e., drug delivery. Other prior art that is geared towards devices for drug delivery to the sinus areas are made by Intersect ENT. These are marketed, for example as the Propel® drug eluting devices (U.S. Pat. Nos. 9,568,681; 7,691,094; 20140276408). These devices are much different than the expanding sponges of our copending U.S. patent application Ser. No. 15/266,659, DEGRADEABLE OSTIAL STENT, filed 16 Sep. 2017 (which is incorporated herein by reference in its entirety). They are like mini crowns that are made of polymer with the drug dispersed within the polymer. The crown is kept compressed and when it is placed, it is allowed to expand. The drug diffuses out of the crown and the crown eventually degrades. Its structure is totally different than that of the present invention, but there are similarities again because of the anatomical regions they are placed and the ability to provide drug delivery.

SUMMARY OF THE INVENTION

A temporary polymeric medical implant with a protective cover for insertion into mammalian ostia includes:
- a polymeric implant having a length, an outer surface with a first diameter, and a cross-section;
- an aqueous-removable protective cover in contact with and over the outer surface of the polymeric implant;
- the aqueous-removable protective cover temporarily maintaining the dimensions of the implant against forces of expansion;
- the protective cover being at least one of biocompatible and frangible, bioabsorbable, aqueous soluble, or biodecomposable such that it may be easily removed;
- the polymeric implant comprising a first aqueous-swellable, biocompatible and bioabsorbable, aqueous soluble, or biodegradable polymer having a thickness;
- the aqueous-swellable, biocompatible and biodegradable polymer implant retaining structural integrity for at least one hour when swollen and kept moist by a moist aqueous environment, and the first diameter expands by at least 15% when water is absorbed therein as compared to the first diameter of the polymeric stent in its dry state.

A hand held tool is used for placement and hydration of an ostial stent comprising the temporary polymeric medical implant with a protective cover. Both the cover and the implant may be made of natural, synthetic or modified natural polymers having the appropriate swelling and fracture properties (even where intentional structural weakening is designed into the cover). The tool has multiple sections and elements. In one embodiment, the tool is comprised of a blunt needle with a plumbing connection at the proximal end (i.e., a luer fitting) for delivery of fluids or suspensions to the lumen of the needle and ultimately to the stent when placed in the target anatomy. The stent with a protective cover is to be placed over the distal end of the tool, and a stop (comprised of a bend, an increased cross section, or a transition in surface roughness) may be present at the distal end of the tool to locate the stent. The distal end of the tool may be bent to allow improved access to the ostia for placement of the stent; typical angles for accessing the frontal and maxillary sinus ostia are 70 degrees and 115 degrees, though angles from zero to 180 degrees are possible and are included within the scope of the invention. The tip of the blunt needle may be sealed shut and perforations may be created around the periphery of the needle in the vicinity of the tip to deliver fluids radially to the stent and to provide a combination of pressure and hydration to disrupt the protective cover, thus allowing the stent to expand and become anchored by the surrounding anatomy.

A polymeric stent comprises a polymeric body having a length, an outer surface and a cross-section. The body may be a continuous dense polymeric matrix or may be a continuous foam structure Alternatively, a lumen passes through part of the device or through the entire length, the lumen having a surface that is an internal equivalent diameter of the polymeric body. The polymeric body includes a first aqueous-swellable, biocompatible and biodegradable polymer matrix having a thickness. The aqueous-swellable and biodegradable polymer matrix retains structural integrity for up to thirty days when swollen and kept moist by a moist aqueous environment. The geometric or non-geometric shape of the polymeric body may be optimized to fit the surrounding anatomy and may take any one of a variety of shapes including but not limited to cylinders, rectangles, triangles, cones, star shapes, rhomboids, and/or random undefined shapes. Similarly, the lumen may be in shapes including but not limited to cylinders, rectangles, triangles, cones, star shapes, rhomboids, and/or random undefined shapes. Barrier layers of biodegradable polymer matrices may be used to prevent migration of liquids into the lumen; said layers may have the additional features of being elastic and/or aqueous-swellable, being capable to lend structural support to the stent, and having variable and tunable degradation rates.

BRIEF DESCRIPTION OF THE FIGURES

FIG. 1A is a perspective of a device (which may be used as to carry an ostial stent, not shown).

FIG. 1B is a perspective of the tip of a device that may be used to carry an ostial stent (not shown).

FIG. 1C is a perspective of the tip of a device that may be used to carry an ostial stent with delivery holes around the periphery of the device near the tip as shown in the figures, providing the hydrating liquid from below.

FIG. 2A is a perspective of an ostial stent that could be used with the device shown in FIG. 1C, that ostial stent includes a swollen foam, a lumen, and a barrier layer.

FIG. 2B a perspective similar to the ostial stent in FIG. 2A, but with differently located barrier layer.

FIG. 3A is a perspective of a compressed foam stent with a plurality of lumens, where the said lumens are completely collapsed.

FIG. 3B is a perspective of a compressed foam with a plurality of lumens that are collapsed or at least partially open and further expand or remain open upon expansion of the compressed foam via addition of a liquid.

FIG. 3C is a perspective of an altered device that includes a swollen foam with a plurality of lumens that pass all the way through the device and a lumen that terminates to produce a blind hole in the device.

FIG. 4A shows a side view of the location of a non-swollen device comprised of a compressed foam with a central lumen inside a narrowing in the human body and not in contact with the surrounding anatomy.

FIG. 4B shows a side view of a device that includes both a foam that has been swollen via the addition of a fluid and a central lumen.

FIG. 6A shows the applicator tool of FIG. 6 from a side view.

FIG. 6B shows an applicator tool tip from the applicator tool of FIG. 6 from a side view.

FIG. 6C shows the applicator tool of FIG. 6 from a front view, with direction of flow of dispensed liquids and solids indicated.

FIG. 9A is a frontal applicator tool, bottom view.

FIG. 9B is a frontal applicator tool, side section view.

FIG. 9C is an applicator tool tip, section view.

DETAILED DESCRIPTION OF THE INVENTION

Figure 2:
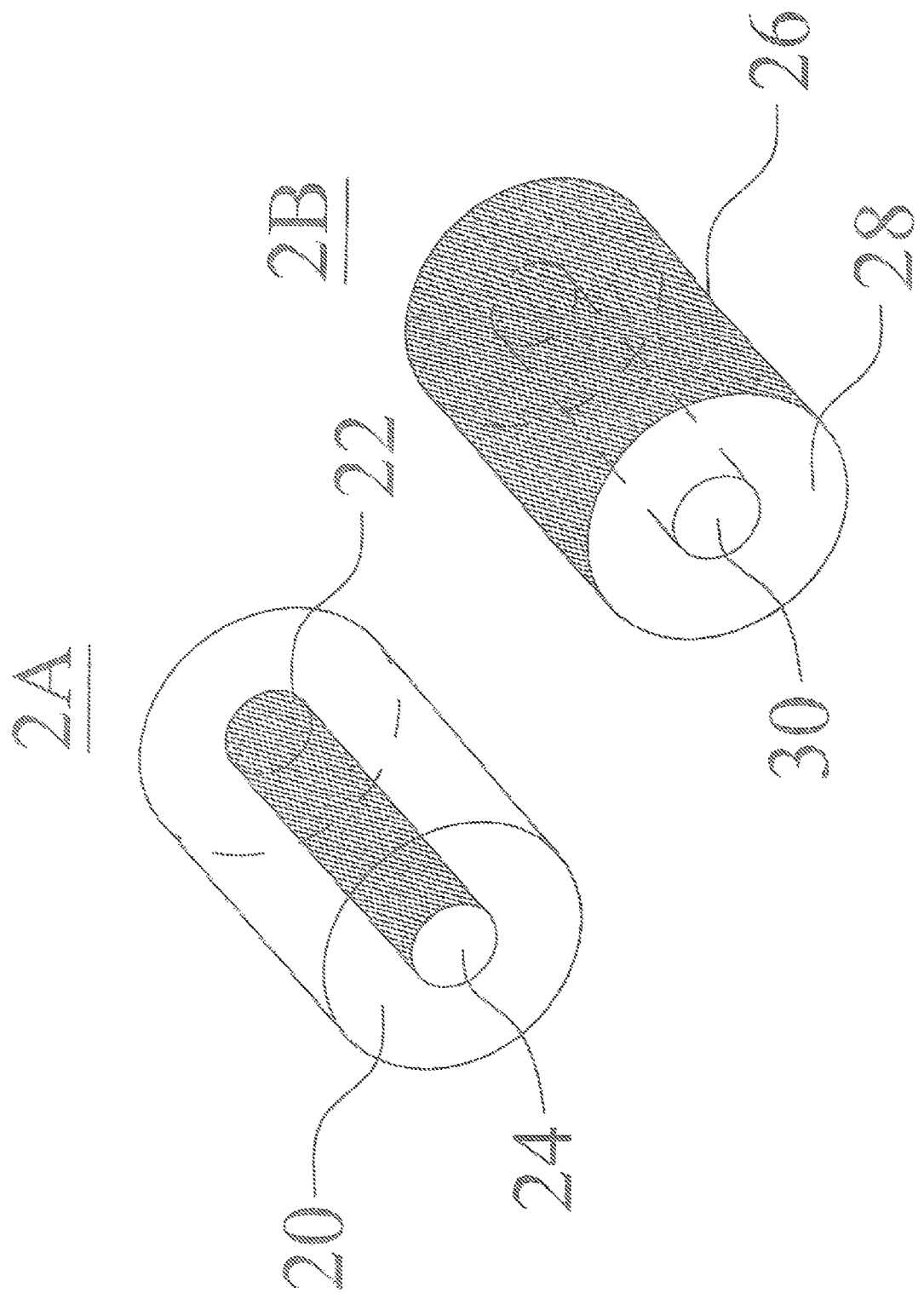
FIG. 2 includes FIGS. 2A and 2B.

The present invention includes an improvement over the technology of the patents (specifically U.S. Pat. No. 10,265, 201) and applications in the Related Application Data section above, and includes a temporary polymeric medical implant with a protective cover for insertion into mammalian ostia comprising:
    a polymeric device (tube, cannula, stent, etc.) having a length, an outer surface, a first diameter and a cross-section;
    an aqueous-removable protective cover in contact with and over the outer surface of the polymeric device;
    the aqueous-removable protective cover temporarily maintaining the dimensions of the polymeric device against forces of expansion;
    the protective cover being biocompatible and at least one of frangible, bioabsorbable, aqueous soluble or bio-decomposable;

the polymeric device comprising a first aqueous-swellable, biocompatible and bioabsorbable, water soluble, or biodegradable polymer having a thickness; the aqueous-swellable, biocompatible and biodegradable polymer retaining structural integrity for at least one hour when swollen and kept moist by a moist aqueous environment, and the first diameter expands by at least 15% when water is absorbed therein as compared to the first diameter of the polymeric stent in its dry state.

One specific focus of the design and structure and function for the stent in U.S. Pat. No. 10,265,201 went into the creation of a polymeric sheath integral to the tool that could protect the implant or inserted stent device from premature hydration during placement and could move relative to the internal shaft to expose the implant or device when it was properly located. By contrast, the present invention allows for an alternative design that does not require a shaft to move relative to a surrounding sheath. Rather, one aspect of improvement for the present implant or device is that it sits on the tip of the insertion tool and is covered by a sheath that protects the present implant during placement and then the sheath dissolves or fragments when supplied with a hydrating liquid, thus allowing the device to expand and conform to the surrounding anatomy in place. The protective cover/sheath is of such resilience that if it comes into contact with bodily fluids upon insertion to the target ostia, as can be expected when inserting a device into a surgical site with blood present, it will maintain its structure and protective function. The structure and protective nature of the sheath is only disrupted upon the purposeful hydration of the stent.

The preferred embodiment of the device includes the fluid and or fluid and solid (suspension) delivery holes around the periphery of the device near the tip as shown in the figures, providing the hydrating liquid from below the protective cover or sheath.

The above implant may have the protective cover/sheath comprised of a film material selected from one or more members in the group consisting of natural polymers, modified natural polymers, synthetic polymers, natural film-forming materials, and synthetic film-forming materials.

The above implant may have the protective cover/sheath comprised of an aqueous soluble, aqueous dispersible, or aqueous degradable organic material or mixture of materials. The above implant may have the protective cover/sheath further comprise designed imperfections (e.g., pores, striations, serrations, cracks) or leachable organic or inorganic substances facilitating physical disruption of the protective cover when hydrated. The protective cover/sheath may assume various geometries including tubes, sleeves, envelopes, etc. depending upon the target anatomy and may be open on multiple faces, a single face, or closed on all faces. Further, the protective covering may closely match the exterior geometry of the device, or it may be larger than the device in one or more directions to afford extra protection for the device, facilitate positioning of the device in the target anatomy, or provide some other beneficial property to the device. The protective cover may be incorporated directly with the tool, primarily in contact with the device but in contact with the tool, or surrounding the device but not in direct physical contact with the tool.

The above implant may be carried on a hand-held device for insertion of a polymeric stent into the ostium of a mammal, including a human being comprising:
  a) a needle with an included angle of >11 (sharp) to 90 degrees (blunt) at the distal tip;
  b) a physical stop to locate a stent placed on the device;
  c) an optional surrounding shaft to stiffen the needle as necessary;
  d) an optional restriction at the tip of the needle to prevent or limit the flow of one or more fluids or a mixture of one or more fluids and one or more solids from the tip when supplied to the needle;
  e) perforations, holes, slits, or other defects at select locations around the circumference of the tool to facilitate radial flow of one or more fluids or a mixture of one or more fluids and one or more solids into the stent when the needle is so supplied.

A hand held tool according to the technology of the patents and applications in the Related Application Data section above, are included within the practices of the present invention for placement and hydration of an ostial stent, and especially a proprietary ostial stent of the inventors in any ostia of a mammal. The tool has multiple sections and elements. In one embodiment of the invention the needle is made of stainless steel, although other rigid materials, metallic or polymeric are acceptable. A key aspect of this invention is that the polymeric stent needs to be protected from exposure to aqueous fluids prior to placement, to prevent it from prematurely expanding due to hydration. The protective cover of the invention is designed to perform this function. The protective cover may be integrated into the tool or integrated into the stent itself.

The invention includes a method of maintaining an open ostium. This is done by inserting into the ostium a polymeric stent using a hand-held device for insertion and/or hydration of a polymeric stent into the ostium of a human being including:
  a) a needle with an included angle of >11 to 90 degrees at the distal tip;
  b) a physical stop to locate a stent placed on the device;
  c) an optional surrounding shaft to stiffen the needle as necessary which may sever as the aforementioned physical stop;
  d) an optional restriction (such as a weld, plug, small orifice, or porous structure) at the tip of the needle to prevent or limit the flow of one or more fluids or a mixture of one or more fluids and one or more solids from the tip when supplied to the needle;
  e) perforations, holes, slits, or other defects at select locations around the circumference of the tool to facilitate radial flow of one or more fluids or a mixture of one or more fluids and one or more solids into the stent when the needle is so supplied.;
  wherein the wherein the tool caries a polymeric ostial stent, the method comprising:
  1) Inserting the tool into the nasal cavity of a human being, advancing the polymeric ostial stent into the ostium by movement of the tool, hydrating the stent and protective cover with an aqueous liquid via the tool if desired causing the protective cover to lose mechanical strength allowing the stent to expand and conform to the surrounding anatomy, and withdrawing the hand-held device while leaving the polymeric ostial stent within the ostium. The protective cover in its disrupted state may also be left in the ostium.

There are numerous different ostia within the body of a mammal, including a human being, in which the present technology can be practiced. It is preferred that the ostia having a direct and natural opening to the exterior of the mammal, such as the nasal passages, urinary passages, ear passages, anus, tear ducts and the like, so that incisions do not have to be made. Such ostia include, but are not limited to:

ostium abdominal—the fimbriated end of the fallopian tube.
ostium cardiacum—the orifice between the esophagus and the stomach.
coronary ostium—either of the two openings in the aortic sinuses that mark the origins of the left and right coronary arteries.
ostium internum ostium uterinum tubae.
ostium pharyngeum the nasopharyngeal end of the eustachian tube.
ostium primum—an opening in the lower portion of the membrane dividing the emb ryonic heart into right and left sides.
ostium secundum an opening in the upper portion of the membrane dividing the embryonic heart into right and leftsides, appearing later than the ostium primum.
tympanic ostium (ostium tympánicum) the opening of the eustachian tube on the carotid wall of the tympanic cavity.
ostium uteri the external opening of the cervix of the uterus into the vagina.
ostium uterinum túbae the uterine end of the fallopian tube; the point where the cavity of the tube becomes continuous with that of the uterus.
ostium vaginae the external orifice of the vagina.
ostium of the maxillary and frontal paranasal sinuses.

Hydration of the stent may also be achieved per the surgeon's expertise and choice of tools, or the stent may be hydrated via the presence of body fluids alone with sufficient time. Although the term "stent" is used in much of the discussions herein by way of example, the device can be a sponge (intended to absorb materials or release and absorb materials as in an equilibrium), wick (to pick up and transfer liquids within the ostium, delivery systems for drugs and medications) and do not require the strength and structural permanence that a stent requires, even when those are also soluble or disruptable (as is the protective cover/sheath on the implant of the present technology).

The section of the needle that caries the stent may protrude beyond the outer edge of the stent in the case that the stent possesses a lumen that passes through the entire length of the stent. Alternatively, the needle may be located inside the stent, whether the stent includes a blind hole or a lumen that passes all the way through the length of the stent. Retention of the stent on the tip of the tool may be facilitated by friction between the internal diameter of the stent and the outer diameter of the carrying needle or some attractive force, and the carrying needle may have a variable or constant cross section. Upon hydration of the stent, dilation of the stent internal diameter, and/or reduced friction between the stent and the tool, and/or reduction in attractive forces between the tool and the stent may facilitate removal of the stent from the tool.

FIGS. 5A, 5B, 5C, 5D, 5E and 5F shows a side view of a bent tool with a stent carried thereon. In all of the figures, identical numbers represent identical elements as follows:
500: Delivery tool for placement and hydration of the device in an ostia (not shown).
502: Side view of the distal tip of the delivery tool.
504: Luer hub connected to an inner tube for supply of fluids and solids to the distal end of the tool.
506: Straight or slightly curved arm of the delivery tool comprised of an outer tube containing an inner tube of lesser diameter.
510: Curved section of the tool to facilitate access to the ostia for placement of the device.
512: Tool stop to properly locate the device during installation on the tool.
514: Device in place on the distal tip of the tool;
520: Solid wall of the device delivery tool.
522: Lumen in the tool for delivery of fluids with or without solids to the distal tip of the tool.
524: Section of the distal tip of the tool.
526: Section of the distal tip of the tool that carries the device prior to deployment in the ostia; in this embodiment the needle is blunt and has a square tip with a 90 degree angle, though other angles down to greater than 11 degrees are possible.
528: Openings in the wall of the tip to facilitate delivery of fluids with or without solids to the device.
530: Stop to locate the device relative to the delivery openings through the wall of the tip. This section of the outer tube is contiguous with the more proximal section of the outer tube and is differentiated only to highlight its special purpose in the design.
532: Curved section of the tool to facilitate access to the ostia for placement of the device. This section of the outer tube is contiguous with the more proximal section of the outer tube and is differentiated only to highlight its special purpose in the design.
534: Straight or slightly curved arm of the tool comprised of an outer tube containing an internal needle of lesser diameter; here, the outer tube adds stiffness and transitions to around the curved tip to provides a built in stop for location of the device on the tool.
536: Protective cover/sheath overlying the expanding portion of the device;
538: Restriction at the tip of the tool to promote radial flow from the perforations around the circumference of the tip;
540: Expanding portion of the device that conforms to the surrounding anatomy upon placement and hydration;
542: Close up of the distal end of the tool highlighting the included angle of the needle, which may vary between blunt (90 degrees) and sharp (12 degrees)

Figure 5:
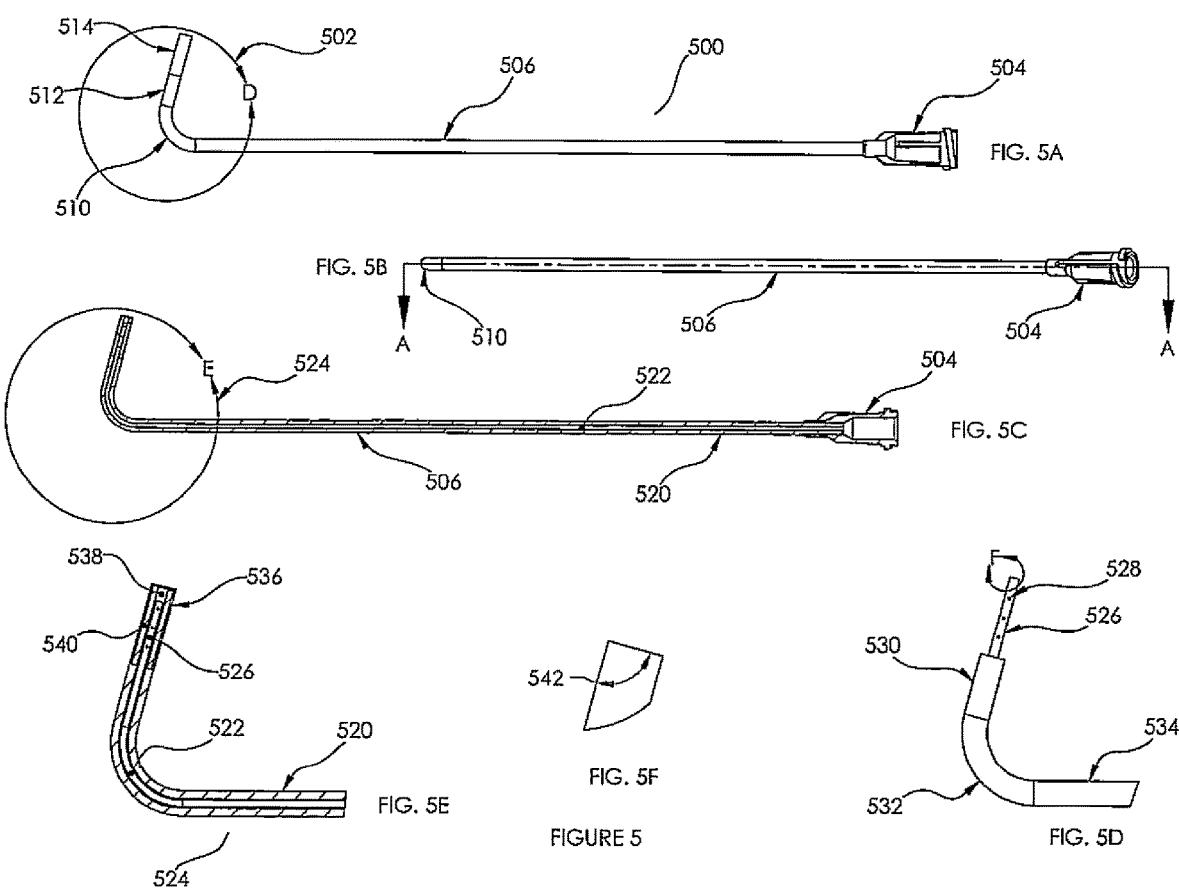
FIG. 5A shows a side view of a bent tool with a stent carried thereon.
FIG. 5B shows a bottom view of a bent tool with a stent carried thereon.
FIG. 5C shows a side cutaway view of a bent tool with a stent carried thereon.
FIG. 5D shows a side view of a bent tool with without a stent carried thereon and the vent holes exposed.
FIG. 5E shows a side cutaway view of an end of the bent tool with a stent carried thereon and the vent holes exposed.
FIG. 5F shows the included angle at the tip of the needle.

FIG. 5B shows a bottom view of a bent tool with a stent carried thereon.

FIG. 5C shows a side cutaway view of a bent tool with a stent carried thereon and the end segment circled for enlargement in FIG. 5E.

FIG. 5D shows a side view of a bent tool with a stent removed which had been carried on the vented 526 end carried of the tool 500 thereon and the vent holes 528 exposed.

FIG. 5E shows a side cutaway view of an end of the bent tool with a stent carried thereon and the vent holes exposed. The hydrating liquid carrier 522 is relatively centered. The stop for location of the stent on the tool is relatively shown as 512 or 530 in FIG. 5D.

The protective cover/sheath protects the stent from premature exposure to water or aqueous material (e.g., mucous and blood), which would cause the ostial stent to absorb water and expand. The protective cover/sheath should be sterile or sterilizable. A lubricious, slippery, low friction surface on the protective cover, or a low friction, lubricious polymer (such as but not limited to polyglucosamines or water soluble celluloses or polyethylene oxide) is preferred.

A preloaded device (with the stent on the tool) is one product, with the tool disposable. This reduces the need for sterilization of the used product. To save some long-term material costs, the tool may be reused (after sterilization).

The tool should have sufficient rigidity to enable the needle to navigate the tight space and not be deflected by the nasal tissues, such as the turbinates, in route to the surgical site. If necessary and outer tube may be placed coaxially tot eh needle to improve rigidity.

The device may have subtle differences within the generic scope of the invention where differentiating between use for the frontal sinus ostia and maxillary sinus ostia. When addressing the frontal ostia, the tip will tend to be bent more gradually between 45 and 85 degrees, most likely between 60 and 80 degrees, with about 70 degrees as a target. When addressing the maxillary ostia, greater and more acute bend is needed, such as between 90 degrees and 135 degrees, more particularly between 100 and 120 degrees, with about 110 degrees a target of the bend in the flexible tip.

A surgeon can perform the procedure by placing the tip of the tool that already has a preloaded polymeric ostial stent inside of the ostia. The polymeric ostial stent is delivered into the ostia when the surgeon supplies the tool with one or more fluids, including an aqueous liquid, or a mixture of one or more fluids, including an aqueous liquid, and one or more solids, causing the protective cover to rupture and the foam to expand and conform to the surrounding anatomy.

For clarity, in the description below and in reference to FIGS. 1 through 4, the protective cover/sheath is omitted from the description. A polymeric stent according to the present inventive technology shall be described heretofore as a cylindrical polymeric tube with a cylindrical lumen, with the understanding that a multitude of other shapes are possible as previously described. The polymeric tube may have a length, an outer surface and a cross-section, with a lumen passing through the entire length. The lumen has an outer surface forming a diameter that is an internal diameter of the cylindrical polymeric tube. The polymeric tube is constructed from a first aqueous-swellable, biocompatible and biodegradable polymer or mixture of such polymers having a thickness. The aqueous-swellable and biodegradable stent should retain structural integrity for up to thirty days when swollen and kept moist by a moist aqueous environment. By structural integrity it is meant that the cylindrical polymeric tube remains capable of supporting the lumen in an open condition, allowing fluid flow there through for the designated time period (three days, five days, 7 days, ten days, etc,). By being biodegradable it is meant that the composition of the tube structure deteriorates into absorbable, dissolvable, dispersible or decomposable size materials so that the tube materials do not persist in the body to any harmful degree. Aqueous soluble or dispersible materials are good examples of materials that break down into small, body dispersible particles sizes, such as less than millimeter diameters, and even to micron-size and/or submicron diameters.

The stent may have the internal diameter surface composed of a second biodegradable polymeric composition layer that is less aqueous-swellable than the first aqueous-swellable and biodegradable polymer(s) and the second biodegradable polymeric composition layer having a thickness that is less than 50% the thickness of the first biodegradable polymeric composition layer. The 50% dimension is fairly high in proportions, as the second layer need be only a film structure acting as a barrier layer. The second biodegradable composition layer may afford the stent addition mechanical integrity and may serve to control the rate of liquid and or solute transport into the lumen. The second biodegradable polymeric composition may be of the same chemical nature as the first biodegradable composition (e.g., polyester, acrylic, polysaccharide, starch, and hydrolyzable polymers that break down into biologically harmless chemical units or dissolve under normal conditions in the human body), in which case the second layer may be less swellable due to a relative increase in density, polymer/polymer interactions, or chemical bonds between polymers. Alternatively, the second biodegradable composition may be of a different chemical nature than the first biodegradable composition.

There are significant design considerations in the design of the combination of the polymeric ostial stent and the hand-held device. Space is very tight for these types of procedures so both the tool and the stent needs to be very small. Different tip bend angles needed ~70 degree for frontal, ~110 degrees for maxillary. Treatment of the maxillary ostia is the more difficult position for placement as it is the most space constrained. The size of the polymeric stent prior to its being inserted, i.e., when it is dry, is much smaller than when it is fully hydrated. Typical nasal ostia are in the range of 5 to 6 mm in equivalent diameter (it is not a perfect hole, so the term equivalent is used). The tips of these types of tools need to be on the order of 1-5 mm in size, more preferably 1 mm to 1.5 mm. Thus in order to accommodate the tight confines of both the tool and the human anatomy, the polymeric ostial stent is compressed to reduce its dimensions. In one example of the present invention, the dry diameter is about 5 mm and when compressed, it is reduced to about 1.8 to 1.9 mm. The stent is compressed axially to reduce its over-all length, going from about 10 mm down to 7 mm, more preferably down to 5 mm. Other compression ratios are within the scope of the present invention. The tip of the stent delivery device may have a polymeric ostial stent installed, or the stent may be placed on the tool by the user. The maximum width of the tool at the distal end containing the ~110 degree bend should not be any bigger than about 10 to 20 mm. A typical width for the device in the practice of this technology is between 15 and 17 mm, such as 16 mm, though smaller widths are also possible. The smaller widths are advantageous for placement in tight anatomies.

The stent may further have an outer surface composed of a third biodegradable polymeric composition layer that is less aqueous-swellable than the first aqueous-swellable and biodegradable polymer and the third biodegradable polymeric composition layer having a thickness that is less than 50% the thickness of the first biodegradable polymeric composition layer. The thickness of the third layer is to assist in preventing passage of excess liquid into the lumen or into the body of the cylindrical tube and then into the lumen. The 50% dimension is fairly high in proportions, as the third layer need be only a film structure acting as a barrier layer. The third layer should also be decomposable/degradable, as it would otherwise remain in the ostia where the tubes have been placed. Even though the third layer is of smaller dimensions, it is seldom desirable to leave unnatural materials within human cavities such as the ostia. Some prior art systems have required physical (surgical) removal of the stents, which can often lead to tearing of the tissue that had been previously supported and even protected by the stent. To that end, prior art materials often had to be constructed with critically smooth surfaces to prevent damage on removal and avoid growth of tissue bonding to uneven sites on the prior art stents. As the present stents decompose, their surface characteristics can be less critical.

In alternate embodiments, a barrier layer may be located internally within the splint, such that it is at some location between the internal and external surfaces of the device. In all locations, the barrier layer may constitute a dense polymer layer, or the barrier layer may possess an intrinsic porosity. The barrier layer(s) may or may not be continuous along the corresponding surface of the stent. One or more barrier layers may impart additional structural integrity to the stent in dry and/or wet states for all or a portion of the residence time of the stent in the body. A given barrier layer may degrade at the same or at a different rate than one or more other barrier layers or than the body of the polymeric stent.

The stent may have the first aqueous-swellable and biodegradable polymer matrix degradable by immersion in human mucous for a period of up to 30 days. Depending on specific medical intent, this period may be shorter or longer, and can be controlled by appropriate selection of compositions used.

The stent may be composed wherein the first, second, third or other aqueous-swellable and biodegradable polymer matrices are selected from the group consisting of hydrolysable polymers, aqueous-dispersible, fragmentable and aqueous-soluble polymers, such as cellulosic polymers, polyesters, polysaccharides, starches, sugars, chitosan and chitosan derivatives (these former materials may be partially crosslinked to adjust their desired physical properties) and other materials known in the medical field to be bioabsorbable, as with stitches and other temporary implants. Similarly, the protective cover on the stent may include, but is not limited to, polymers from the aforementioned group.

A method of maintaining an open ostium comprising inserting into the ostium a polymeric stent can include steps in which:
  a cylindrical polymeric tube having a length, an outer surface, a cross-section, with a lumen passing through the entire length, the lumen having a surface forming a diameter that is an internal diameter of the cylindrical polymeric tube is provided;
  the polymeric tube includes a first aqueous-swellable, biocompatible and biodegradable polymer matrix having a thickness;
  the aqueous-swellable and biodegradable polymer retaining structural integrity for at least one hour (for purposes of allowing clotting and protecting a wound), at least six hours, at least one day, at least five days, or even at least up to thirty days (for longer short-term benefits) when swollen and kept moist by a moist aqueous environment, the method further including:
  allowing natural fluids within the ostium to swell the first aqueous-swellable, biocompatible and biodegradable polymer matrix or introducing artificial aqueous solution to swell the aqueous-swellable, biocompatible and biodegradable polymer;
  wherein the swelling expands the cylindrical polymeric tube against tissue within the ostium to secure the cylindrical polymeric tube within the ostium.

The method may allow the cylindrical tube to remain in the ostium and allow natural body fluids to degrade the first biodegradable polymeric composition layer such that integrity of the cylindrical tube is reduced.

The method may further include using a structure wherein the internal diameter surface is composed of a second biodegradable polymeric composition layer that is less aqueous-swellable than the first aqueous-swellable and biodegradable polymer and the second biodegradable polymeric composition layer has a thickness that is less than 50% the thickness of the first biodegradable polymeric composition layer, and allowing the cylindrical tube to remain in the ostium also allows natural body fluids to degrade the second biodegradable polymeric composition layer and degrade integrity of the cylindrical tube is further reduced.

The method may function wherein expanding the cylindrical polymeric tube against tissue within the ostium allows distal ends of the polymeric tube to expand to diameters greater than a middle section of the cylindrical polymeric tube. This provides a bow-tie appearance to the inserted and swollen stent.

A further understanding of the practice of the invention will be appreciated by a review of the Figures.

FIG. 1A depicts a device 100 (which may be used to carry an ostial stent as described herein, not shown) that includes a compressed foam structure (2) and a collapsed lumen that is not visible to the naked eye. A distal bent tip section B is shown. FIG. 1B depicts a bent tip section of the device 100 that also may be used to carry a compressed foam structure (not shown). The devices and bent tip depicted in FIGS. 1A and 1B may carry ostial implants that expand via the addition of liquid to produce an altered device (depicted in FIG. 1C). The tip 102 in FIG. 1C is also shown with vent holes 104.

FIG. 2: FIG. 2A depicts a variant of the ostial implant that may be carried by the device shown in FIG. 1C, that could include an ostial implant that becomes a swollen foam (20) that has expanded via the addition of a liquid, a lumen (24), and a barrier layer (22) designed to control the transport of solvents and solutes along the lumen wall. The device illustrated in FIG. 2B is similar to the device in FIG. 2A, and it has a swollen foam (28) that has expanded via the addition of a liquid and a lumen (30); however, the device in FIG. 2B is different from the device in FIG. 2A, as it has a barrier layer (26) designed to control the transport of solvents and solutes on the outer surface of the device rather than on the lumen.

Figure 3:
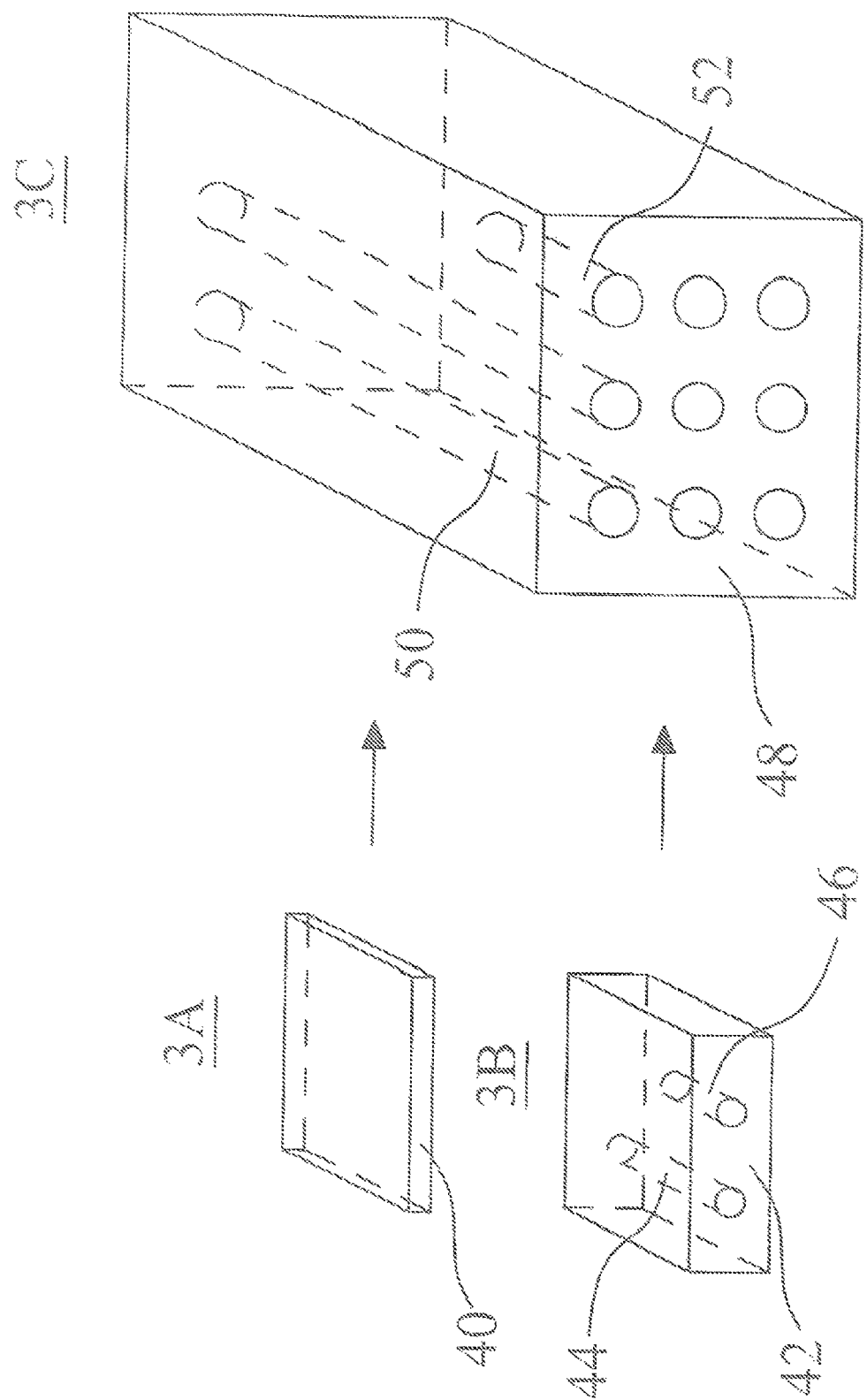
FIG. 3 includes FIGS. 3A and 3B and 3C.
Figure 4:
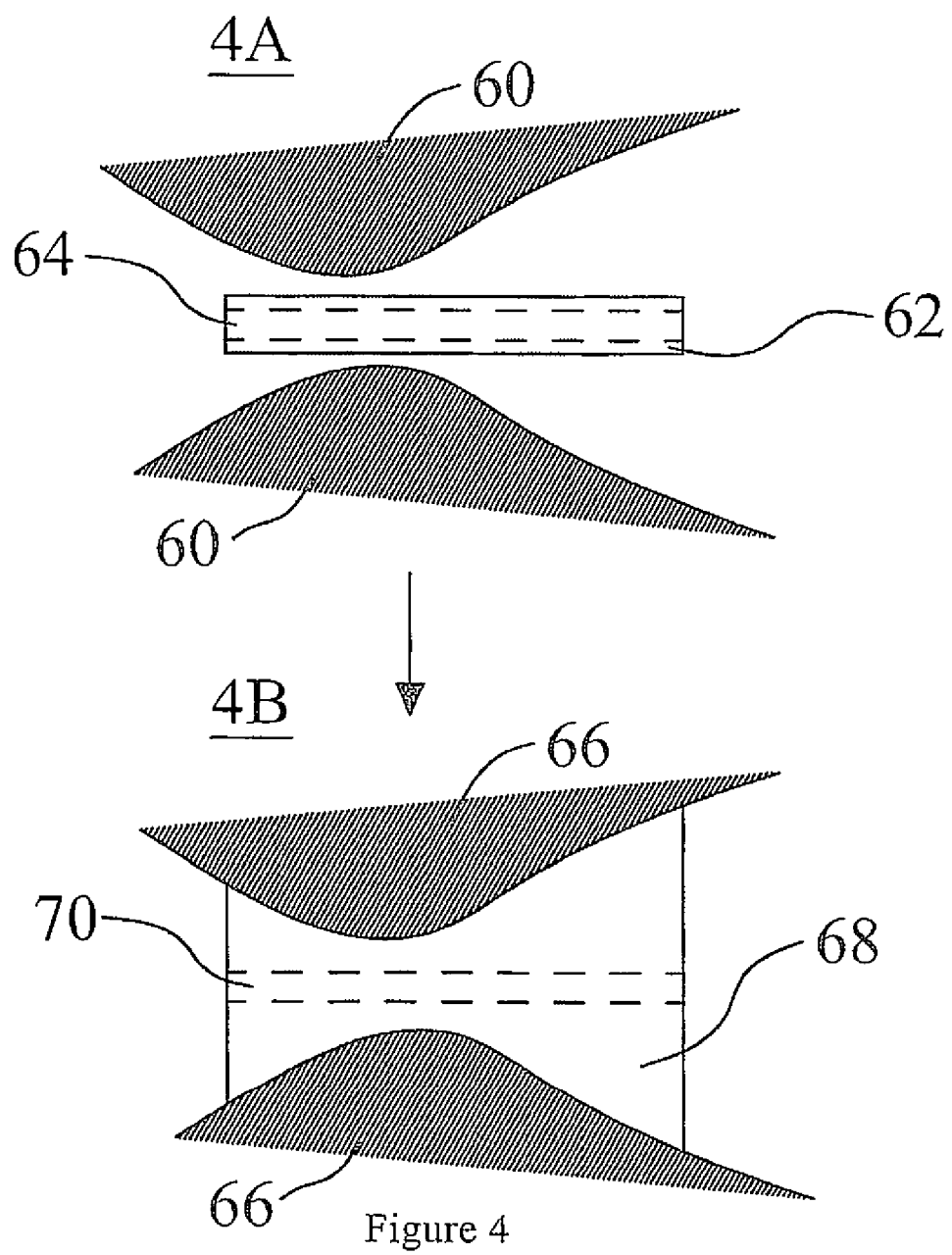
FIG. 4 includes FIGS. 4A and 4B.

FIG. 3 shows alternative foam structures: The device in FIG. 3A includes a compressed foam (40) with a plurality of lumens, where the said lumens are completely collapsed. The device in FIG. 3B includes a compressed foam (42) with a plurality of lumens that are collapsed or at least partially open and further expand or remain open upon expansion of the compressed foam via addition of a liquid. One of the depicted lumens passes all the way through the device in FIG. 3B (44) and one of the depicted lumens terminates part way through the device to produce a blind hole (46). The devices illustrated in FIGS. 3A and 3B expand via the addition of liquid to produce an altered device (depicted in FIG. 3C) that includes a swollen foam (48) with a plurality of lumens that pass all the way through the device (50) and a lumen that terminates to produce a blind hole (52) in the device. The blind hole can be used by the medical practitioner as a delivery port for injecting liquid into the swellable polymeric cylindrical core to preferentially deliver the liquid to the stent and prevent loss of the liquid out of the distal end.

FIG. 4A shows the location of an ostial stent comprised of a compressed foam (62) with a central lumen (64) inside a narrowing in the human body and not in contact with the surrounding anatomy (60). FIG. 4B shows an ostial stent that includes both a foam (68) that has been swollen via the addition of a fluid and a central lumen (70). The swollen foam has expanded to make contact with and conform to the shape of the surrounding anatomy (66) via expansion of the originally compressed device depicted in FIG. 4A.

Other aspects of the technology can be practiced within the practice of the invention as described. Newer synthetic or polymeric materials meeting the described properties can be used. The geometric shape of the polymeric body may be optimized to fit the surrounding anatomy and may take any one of a variety of shapes including but not limited to cylinders, rectangles, triangles, cones, star shapes, rhomboids, and/or random undefined shapes. Similarly, the lumen may be in shapes including but not limited to cylinders, rectangles, triangles, cones, star shapes, rhomboids, and/or random undefined shapes. Longitudinal reinforcement of the various shapes may be used (with biodegradable materials). The dimensions and ratios of the dimensions may be varied. For example, in the case of a cylinder, the ratio of the inside diameter of the lumen to the length of the device on the unswelled device can vary between 1:2 and 1:30, preferably between 1:3 and 1:20. Similarly, the ratio of the inside diameter of the lumen to the outside diameter may vary between 1:1.1 to 1:10 in an unswelled state and from 1:1.5 to 1:20 in a swollen state. Other variations are within the ordinary skill of the designer.

The devices are intended to provide a persistent open lumen through the ostium, and minimize any damage that might occur during removal. In the operation of the tools and temporary implants of the present invention, reference to FIGS. 5A-5E show that the implant or device 514 is in place on the distal tip of the tool 500 and that the tool stop 512 is used to properly locate the implant or device 514 during installation with the tool 500. The implant, such as the post separation sponge 514 is carried on the extended, straight end 526 of the tool 500 and the pores 526 provide hydrating fluid (not shown) and when the post separation sponge 514 has swollen enough to fix itself in its desired position, the end of the tool 528 is withdrawn by complete manual withdrawal of the entire tool 500.

Where the outmost surface (and even the innermost surface) is a barrier layer, it may also be somewhat elastic to allow the polymer to swell. The cylinder shape of the device may also be conical, and the cross-sections (of the body and the lumens) can be any geometric of irregular shape.

A method of maintaining an open ostium comprising providing a hand-held device for insertion of a polymeric stent into the ostium of a human being according to the present invention may include providing a tool of:
  a) a needle that fits inside the lumen of the stent;
  b) a physical stop to locate a stent placed on the device;
  c) the option for a surrounding tube to stiffen the needle as necessary;
  d) the option for a restriction at the tip of the needle to prevent or limit the flow of one or more fluids or a mixture of one or more fluids and one or more solids from the tip when supplied to the needle;
  e) perforations, holes, slits, or other defects at select locations around the circumference of the tool to facilitate radial flow of one or more fluids or a mixture of one or more fluids and one or more solids into the stent when the needle is so supplied The method then includes:
Inserting the tool into the nasal cavity of a human being, advancing the polymeric ostial stent into the ostium by movement of the tool, hydrating the stent and temporary protective cover with an aqueous liquid via the tool if desired causing the protective cover to lose mechanical strength allowing the stent to expand and conform to the surrounding anatomy, and withdrawing the hand-held device while leaving the polymeric ostial stent within the ostium.

The technology disclosed and claimed herein also evidences a method of maintaining an open ostium in a mammal comprising inserting into the implant of the invention using a hand-held device for insertion of the temporary polymeric medical implant into the ostium of the mammal comprising:
  a) a handle;
  b) a guide shaft having a flexible segment towards a distal end of the guide shaft and;
  c) the guide shaft having a lumen and having a bent tip; and
  d) the guide shaft supporting the implant extending from, adjacent to or along the distal end of the guide shaft, the method comprising:
inserting the guide shaft supporting the implant into an ostium of the mammal,
hydrating the implant to swell the implant, and then removing the guide shaft without removing the implant.

The method may have the implant with the aqueous-removable protective cover in contact with and over the outer surface of the cylindrical polymeric tube and hydrating the implant disrupts the aqueous removable cover.

The aqueous removable cover may have physical striations, serrations, or intentional deficiencies in its structure to facilitate disruption as a result of hydration of the implant.

Another way of describing the method is as a process of maintaining an open ostium in a mammal comprising inserting the implants described above into an ostium using a hand-held device for insertion of the temporary polymeric medical implant into the ostium of the mammal comprising:
  a) a handle;
  b) a guide shaft having a flexible segment towards a distal end of the guide shaft and;
  c) the guide shaft having a lumen and having a bent tip; and
  d) the guide shaft supporting the implant extending from, adjacent to or along the distal end of the guide shaft, the method including:
inserting the guide shaft supporting the implant into an ostium of the mammal, hydrating the implant to swell the implant, and then removing the guide shaft without removing the implant.

Other variations in materials and dimensions that are not critical to the general functioning of the technology described herein. Further, the following features add novel and unobvious structural features to earlier variants internally evaluated on this technology.

There can be selective perforation of a soluble sheath surrounding the foam component to promote fracture and dissolution of the sheath at predetermined locations. For example, the distal end of the sheath may be perforated and the proximal end may have comparatively fewer perforations to promote dissolution of the sheath and hydration/expansion of the underlying foam at the distal end prior to the proximal end. The perforations may be varied in size, dependent upon functionality intended to be provided, from adjustment of flexibility, increasing moisture flow through the sheath, speed of dissolution of the sheath, relative rate of dissolution along the length of the sheath, and the like. Larger perforations would allow for faster fluid flow through the sheath and faster dissolution of selected areas of the sheath. By placing openings (or larger openings) only in the distal end of the sheath, the distal end of the medical implant would expand earlier in the process, facilitating conformation to the anatomy and anchoring the implant in zones that are not visible to the surgeon first. The rearward (more proximal) section of the expandable implant would then stabilize upon later dissolution of the sheath. The degree of expansion in the expandable implant need not be different between the distal and proximal end of the expandable implant, but the rate at which the diverse ends expand to a similar (or if desired different) degree is thus controlled.

Perforations may be provided and their size and location provided by many different and available processes. If the sheaths are formed by molding, the mold die may have posts or pins located to create the holes or differential thickness at desired points. If extruded, many more procedures are available. The sheath may be laser perforated, punctured mechanically, be originally formed with striations along its length, the depth of the striations varying by altering extrusion surfaces, and the like. It is to be noted that the term "perforation" includes varying the thickness of the sheath at desired locations and with appropriate intended distributions and does not require complete openings passing through the entire thickness of the sheath. The actual hole or perforation diameters may be, for example, between 0.10 mm up to about 1 cm. The perforations (when present as actual holes) would more typically be from 0.10 mm to 1.5 mm.

The tip of the tool will terminate at some point within the lumen of the foam. Rather than extending through entirely through the length of the foam, the tool may extend only 25%, 40%, 50%, 60%, 75% or up to less than 90% of the length of the foam, with ranges of 25%-90%, 25%-80%, and 40%-75% being generally preferred. This can function to reduce the net contact area between the foam and tool, thereby reducing the frictional force between the tool tip and foam facilitating removal of the tool from hydrated foam.

The foam may include perforations at select positions to reduce the total solids in the foam, increase the hydraulic permeability of the foam, and facilitate the transport of solids outward through the foam structure. These perforations or holes may be formed by the various methods described above for forming perforations in the sheath. In this case, the holes preferably pass all the way through the foam to remove mass from the volume of the foam. The hole sizes and volume removed should not be so great as to destroy the effective expansion forces implemented by the foam. Therefore, removal of more than 75% of the foam is not likely, even with actual hole diameters being relatively small (e.g., 0.25 mm diameter. Hole sizes here (and for the perforations in the sheath may vary significantly, although the holes sizes might tend to be allowed as somewhat larger in the foam. The hole sizes in the foam would most likely be within the range Of 0.20 mm up to about 1 cm, such as between 0.20 mm to 0.75 cm, although as stated above, they could be slightly higher than 1.0 cm if the physical integrity of the foam is not lost. The holes in the foam would tend to be radial in the foam, although more axially oriented holes could be used, but they would tend to reduce the compressive strength of the foam more effectively. Axial holes would be easily formed during extrusion, which offers a manufacturing advantage over post-extrusion perforation techniques.

The foam may be compressed in both the radial and axial directions such that the foam can expand radially and axially to fill the ostia despite a relatively small dry device footprint. Although the emphasis of this technology has focused on radial expansion of the expandable foam device, there are benefits in allowing or enabling the foam to extend lengthwise during the expansion phase, such as filling the entire length of the sinus ostia with a smaller dry footprint. The lengthwise (axial) expansion is provided simply by initially compressing the foam in an axial direction as well as the radial direction. A cover (similar to the sheath) may or may not be placed over the axial ends, as the friction between the sheath and foam would also retard or stop the axial expansion. With an axial and radial compression, the foam re-expands when the restraint of the sheath is removed.

The foam and or sheath may include medicinal and/or antimicrobial agents to mitigate medical conditions or infection upon placement and irrigation in the nose. These "functional ingredients" may be imbibed into the foam, extruded with the foam, coated onto the foam, or otherwise incorporated onto the surface and/or into the body of the foam during manufacture. As one example, the antimicrobial agents may be added to a polymer solution that is lyophilized to build the foam structure and incorporate the antimicrobial agent(s) in a single step. Medicinal ingredients other than antimicrobials would include anti-inflammatants, cauterizing agents, moisturizing agents, numbing agents, and the like. Antimicrobial agents can be antiviral agents, antibiotics, antifungal agents and the like. These antimicrobial agents should be selected on bases including lack of allergenic response by the particular patient. The antimicrobial agents are not limited within the function of the present invention, and the following list is merely exemplary. An antimicrobial agent that is lethal to microbes (especially a viricide) selected from, but not limited to, one or more of: polyhexamethylene biguanide (PHMB), other biguanide compounds, chlorohexidine, alexidine, and relevant salts thereof, a quaternary ammonium compound, a quaternary siloxane, a polyquaternary amine; metal-containing species and oxides thereof, either in particle form or incorporated into a support matrix or polymer; halogens, a halogen-releasing agent or halogen-containing polymer, a bromo-compound, a chlorine dioxide, a thiazole, a thiocynate, an isothiazolin, a cyanobutane, a dithiocarbamate, a thione, a triclosan, an alkylsulfosuccinate, an alkyl-amino-alkyl glycine, a dialkyl-dimethyl-phosphonium salt, a cetrimide, hydrogen peroxide, 1-alkyl-1,5-diazapentane, cetyl pyridinium chloride, stabilized peroxide, sulfides, bis-phenols, polyphenols, chitosan, antimicrobial dyes such as gentian violet and/or methylene blue, anatase $TiO_2$, tourmaline, hydrotropes, chaotropic agents, and synergistic combinations thereof.

The sheath component may include a colored dye to allow efficient perforation and cutting with a laser. The sheath or foam layers which are laser-ablated to form indentations, holes or perforations according to the present invention is preferably a laser disruptable or ablatable layer. In a highly preferred embodiment of the invention the foam or sheath is a laser-ablatable layer. The laser-ablatable layer preferably comprises a heat combustible polymeric layer or binder and a light absorbing compound. The heat-combustible polymeric binder can be decomposed, depolymerized or evaporated without a preceding melting step by the heat generated by the absorbing compound upon laser exposure. For example, the heat-combustible polymeric binder may include carbon-based polymers, and may have readily decomposable groups therein such as nitro groups or nitrate ester groups. Especially nitrate esters of cellulose or cellulose ethers are preferred. More specifically nitro-cellulose is used. The preferred light absorbing compounds are IR-absorbing dyes such as phthalocyanines or derivatives, cyanine dyes, merocyanine dyes and polymethine dyes or inorganic pigments such as carbon black, graphite, iron oxide or chromium oxide. Preferably carbon black is used. Furthermore, carbon black renders the ablatable layer opaque to UV radiation, so there is no need to add an additional UV-absorbing dye, but UV-absorbing dyes may be used in combination with the colored dye or in place of them. It is particularly preferred to use fine-grained carbon black with a mean particle size below 30 nm which is commercially available in the printing industry as Printex™ U, Printex™ L6, Specialschwarz 4™ or Specialschwarz 250™ (all trademarks from Degussa). Heat-absorbing pigments may also be used, but they might impact the core structure of the sheath or foam more than dyes, which can be blended into the sheath or foam compositions during manufacture.

The lumen of the foam component may expand upon hydration to improve release from the tool and to promote air flow through the ostia after deployment. The lumen of the foam maybe tapered to optimize the balance between tool/foam friction in the dry state and ease of release from the tool in the hydrated state. For example, the distal tip may taper down from the thickness at the proximal and middle range of the distal end of the expandable insert. This taper can have a number of benefits, including sealing the distal side of the ostia or nasal cavity gently and effectively. The taper may be relatively smooth or continuous, or may provide a more sinusoidal wave appearance, or may even be segments as with progressively smaller flaps of material.

The tip of the tool may include openings that are at an angle to the long axis of the tip to direct the hydration fluid onto the body of the foam during hydration. Rather than being perpendicular to the axis of the tool and foam, they may be at an angle, such as 15-90 (90 being perpendicular to the axis).

Figure 6:
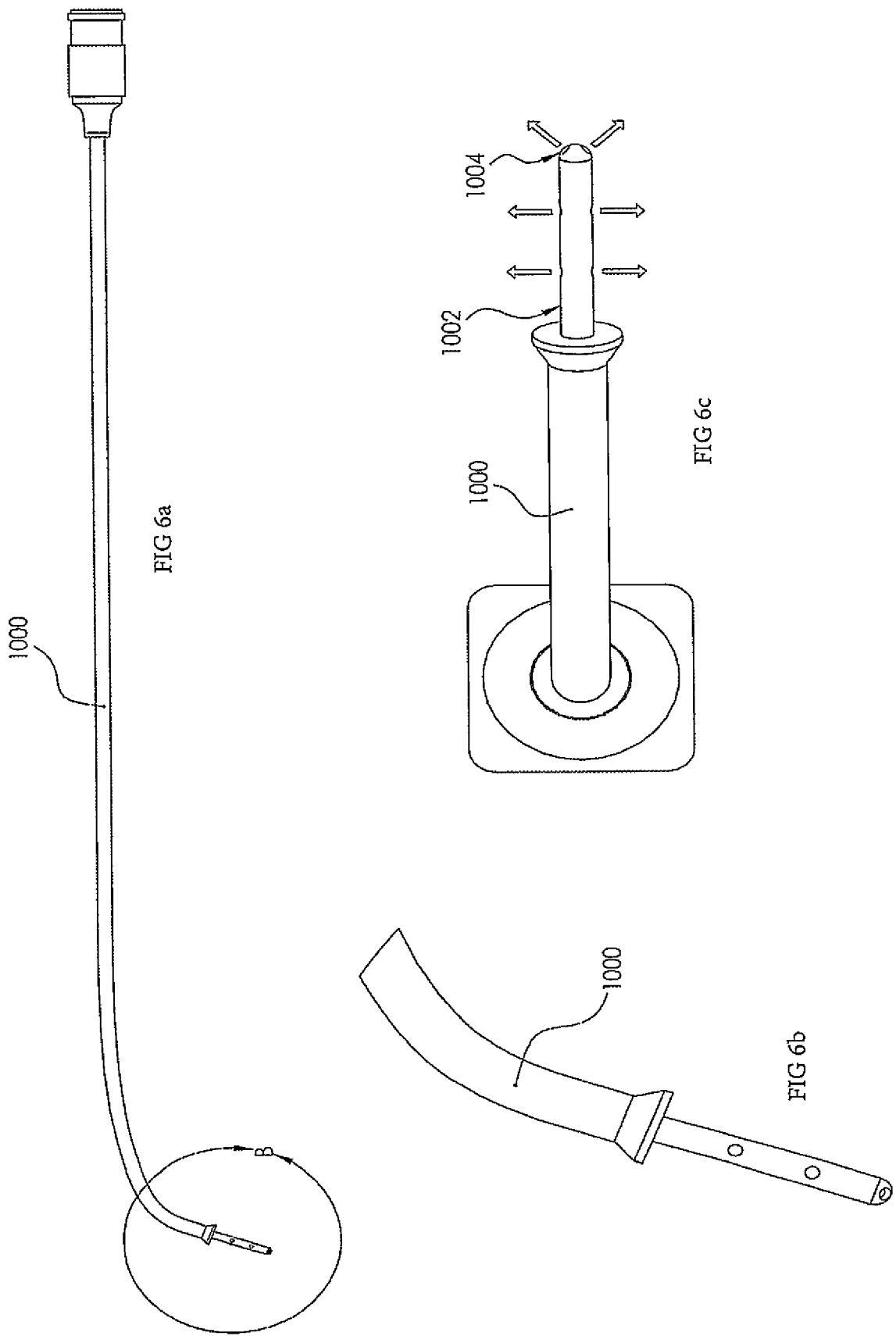
FIG. 6 shows an applicator tool.
Figure 7:
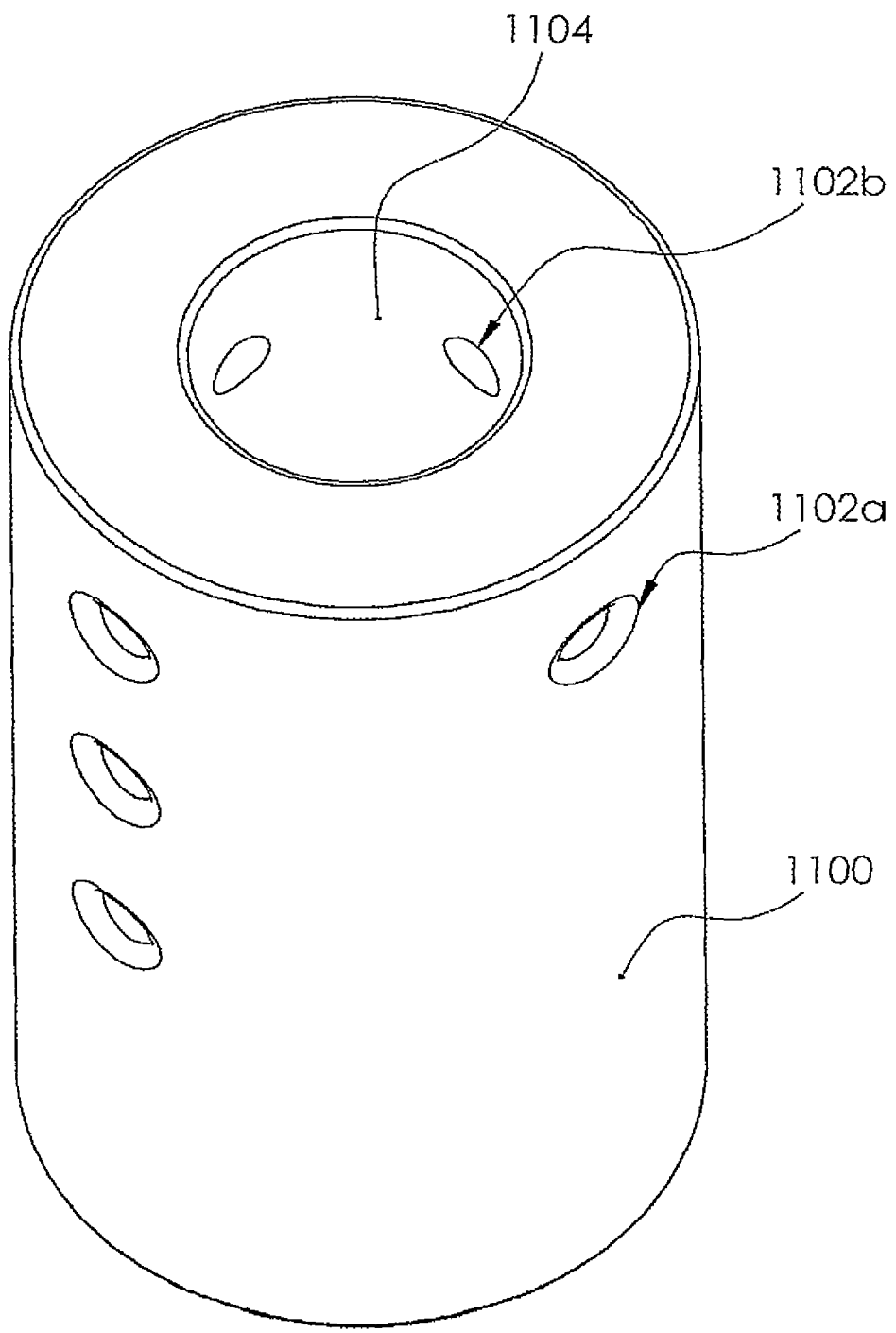
FIG. 7 is an image of an expanded foam tube.
Figure 8:
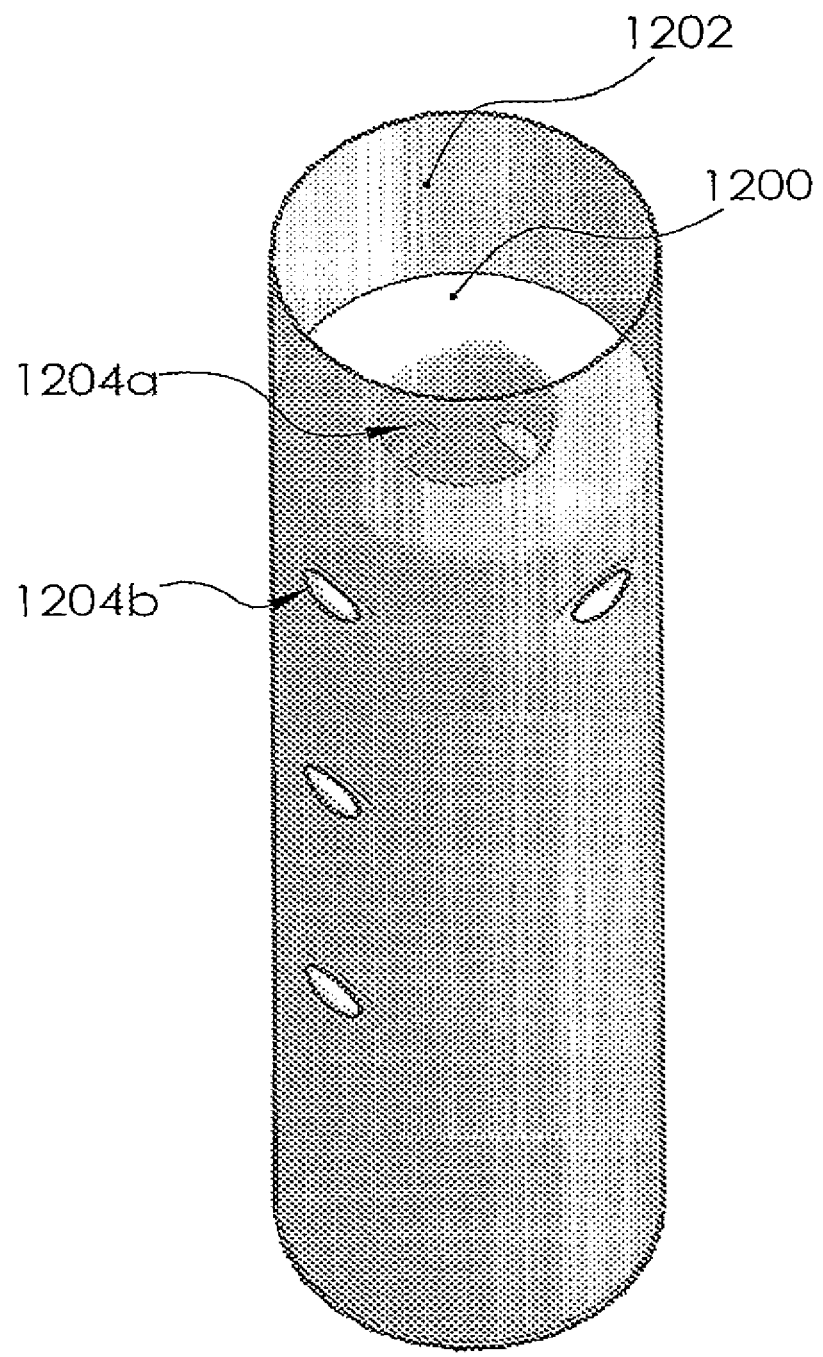
FIG. 8 is a foam compressed and confined by the sheath.

Additional aspects of the generic technology of this invention are exemplified and described further in:
FIG. 6A, 6B, 6C: An Applicator tool
FIG. 6A: Applicator tool, side view
FIG. 6B: Applicator tool tip, side view
FIG. 6C: Applicator tool indicating the direction of flow for dispensed fluids and solids, front view. In these three Figures, the numbering uniformly represents:
1000: Applicator tool needle body
1002: Applicator tool tip with custom-angled axial holes
1004: Axial holes at the distal end of the applicator tool tip. The angle of the axial holes can be customized within a range of 0-90 degrees (as described earlier herein) from the normal vector at the distal end of the tool tip. The dimensions of the holes may be optimized for flow distribution and to prevent plugging during irrigation with a solid/liquid dispersion.
FIG. 7: is an image of an Expanded foam tube
1100: Expanded foam tube
1102a: Perforations in the expanded foam tube. The perforations penetrate the foam walls and terminate in the lumen of the foam. The patterning and sizing of the perforations across the foam tube surface can be customized depending on the desired fluid/solid flow distribution and foam-expansion profile.
1102b: Perforations terminating in the lumen of the expanded foam tube 1100.
1104: Lumen of the expanded foam tube 1100.
FIG. 8: Foam compressed and confined by the sheath
1200: A Compressed foam tube
1202: A Sheath to be over the compressed foam tube 1200
1204a: Perforations terminating within the lumen of the compressed foam tube.
1204b: Perforations in the compressed foam tube and sheath. The perforations penetrate the sheath and foam walls and terminate in the lumen of the foam. The patterning and sizing of the perforations across the sheath and foam tube surface can be customized depending on the desired fluid/solid flow distribution and foam-expansion profile.
FIG. 9A: Frontal applicator tool, bottom view
FIG. 9B: Frontal applicator tool, side section view
FIG. 9C: Applicator tool tip, section view
1300: Frontal applicator tool needle body
1302: Applicator tool tip
1304: Compressed foam tube
1306: Sheath Variations of the shapes and dimensions of the elements of the present technology may be practiced and remain within the scope of this disclosure and the following claims. For example, where holes are shown in the figures as round, they b any other regular or irregular geometric shape without deviating from the practice of the present invention. Materials for the foam, other than those specifically identified may be made from synthetic polymers, elastomers and natural materials by differing processes, including blow agents during shaping of the foam, blending gas into the polymer to form bubbles before hardening the foam, or mechanical penetration and opening of the material may be effected.

Metal and plastic structural components may be used for structural elements, and even composites or ceramics may be used where (in the latter case) flexibility is not required.

What is claimed:

1. A method of maintaining an open sinus ostium in a mammal using a polymeric medical implant comprising an aqueous swellable and biodegradable polymer, the temporary medical implant being a nasal ostial implant comprising:
   a) an aqueous-removable protective cover;
   b) a cylindrical polymeric tube having a length, an outer surface with a first diameter, and a cross-section;
   c) the aqueous-removable protective cover in contact with and positioned over the outer surface of the cylindrical polymeric tube;
   d) the aqueous-removable protective cover maintaining the dimensions of the nasal ostial implant against forces of expansion, the aqueous-removable protective cover being biocompatible and disruptable by hydration;
wherein the nasal ostial implant is attached to a tool comprising; and
   e) a guide shaft having a distal end of the guide shaft and the guide shaft having a lumen and having a bent tip; and
   f) the guide shaft supporting the nasal ostial implant extending from, adjacent to or along the distal end of the guide shaft; and
wherein the method comprises
   g) using the guide shaft to insert the nasal ostial implant into the mammalian ostium;
   h) inserting the guide shaft with the bent tip while the guide shaft is supporting the nasal ostial implant comprising the aqueous swellable and biodegradable polymer into the sinus ostium of the mammal;
   i) hydrating the aqueous-removable protective cover in contact with and positioned over the outer surface of the cylindrical polymeric tube to disrupt the aqueous-removable protective cover and allow the nasal ostial implant to expand;
   j) hydrating the implant to swell the nasal ostial implant, and then removing the guide shaft without removing the implant, the first diameter expanding by at least 15% when water is absorbed therein as compared to a first diameter of the polymeric tube in a dry state;
   k) the aqueous-swellable and biodegradable polymer remaining in the mammalian ostium for at least one hour after insertion into the mammalian ostium and after being swollen and kept moist by a moist aqueous environment within the mammalian ostium; and
   l) the nasal ostial implant biodegrading.

2. A method of maintaining an open sinus ostium in a mammal having a sinus ostium using a polymeric medical implant comprising an aqueous swellable and biodegradable polymer, the implant being a nasal ostial implant comprising:

a) an aqueous-removable protective cover;
b) a cylindrical polymeric tube having a length, an outer surface with a first diameter, and a cross-section;
c) the aqueous-removable protective cover in contact with and positioned over the outer surface of the cylindrical polymeric tube;
d) the aqueous-removable protective cover maintaining the dimensions of the nasal ostial implant against forces of expansion, the aqueous-removable protective cover being biocompatible and disruptable by hydration;
e) a guide shaft having a distal end of the guide shaft and the guide shaft having a lumen and having a bent tip; and
f) the guide shaft supporting the nasal ostial implant extending from, adjacent to or along the distal end of the guide shaft;
wherein the method comprises
   i) inserting the nasal ostial implant into the mammalian sinus ostium;
   ii) inserting the guide shaft with the bent tip while the guide shaft is supporting the nasal sinus ostial implant comprising the aqueous swellable and biodegradable polymer into the sinus ostium of the mammal;
   iii) hydrating the aqueous-removable protective cover in contact with and positioned over the outer surface of the cylindrical polymeric tube to disrupt the aqueous-removable protective cover and allow the nasal ostial implant to expand;
   iv) hydrating the implant to swell the nasal ostial implant, and then removing the guide shaft without removing the nasal ostial implant, the first diameter expanding by at least 15% when water is absorbed therein as compared to a first diameter of the polymeric tube in a dry state;
   v) the aqueous-swellable and biodegradable polymer remaining in the mammalian nasal ostium for at least one hour after insertion into the mammalian sinus ostium and after being swollen and kept moist by a moist aqueous environment within the mammalian sinus ostium; and
   vi) the nasal ostial implant biodegrading.

3. The method of claim 2 wherein the nasal ostial implant has the aqueous-removable protective cover in contact with and over the outer surface of the cylindrical polymeric tube and hydrating the nasal ostial implant to disrupt the aqueous removable cover.

4. The method of claim 3 wherein the aqueous removable cover has physical striations, serrations, or intentional deficiencies in its structure to facilitate disruption of the aqueous-removeable cover as a result of hydration of the aqueous-removeable cover.

5. The method of claim 2 wherein the distal end of the guide shaft is bent at angles between 0 and 180 degrees, the method further comprising:
   inserting the bent distal end of the guide shaft supporting the nasal ostium implant into the ostium of the mammal, hydrating the implant to swell the nasal ostium implant, and then removing the guide shaft without removing the nasal ostium implant.

6. The method of claim 5 wherein the aqueous removable cover has physical striations, serrations, or intentional deficiencies in its structure which facilitate disruption of the aqueous-removeable cover as a result of hydration of the aqueous-removeable cover.

7. The method of claim 2 wherein the nasal ostial implant is carried on a hand-held device and inserted by the hand-held-device into the ostium of a human being comprising, and the hand-held-device further comprises:
   g) a blunt needle; and
   h) a physical stop to locate the ostial implant placed on the hand-held device.

8. The method of claim 7 wherein the nasal ostial implant further comprises at least one of A) a surrounding shaft to stiffen the blunt needle as necessary; B) perforations, holes, slits, or other defects at select locations around the circumference of the blunt needle to facilitate radial flow of one or more fluids or a mixture of one or more fluids and one or more of the solids into the nasal ostial implant when the needle is so supplied.

9. The method of claim 2 wherein the protective cover comprises an aqueous soluble, aqueous dispersible, or aqueous degradable organic material.

10. The method of claim 2 wherein the tip at the distal end of the guide shaft is bent between 70 degrees and 115 degrees when the tip is inserted into the sinus ostium of the mammal.

11. A method of maintaining an open sinus ostium in a mammal having a sinus ostium using a polymeric nasal ostial implant comprising an aqueous swellable and biodegradable polymer, the nasal ostial implant comprising:
   a) an aqueous-removable protective cover,
   b) a cylindrical polymeric tube of the aqueous swellable and biodegradable polymer having a length, an outer surface with a first diameter, and a cross-section;
   c) the aqueous-removable protective cover being in contact with and positioned over the outer surface of the cylindrical polymeric tube;
   d) the aqueous-removable protective cover maintaining the dimensions of the nasal ostial implant against forces of expansion, the aqueous-removable protective cover being biocompatible and disruptable by hydration;
   e) a guide shaft having a distal end of the guide shaft and the guide shaft having a lumen and having a bent tip bent between 70 and 115 degrees; and the guide shaft supporting the implant extending from, adjacent to or along the distal end of the guide shaft;
wherein the method comprises
   i) manually supporting the guide shaft;
   ii) manually inserting the nasal ostial implant into the mammalian sinus ostium using the guide shaft;
   iii) inserting the guide shaft supporting the nasal ostial implant into the sinus ostium of the mammal with the bent tip on the guide shaft;
   iv) hydrating the aqueous-removable protective cover in contact with and positioned over the outer surface of the cylindrical polymeric tube to disrupt the aqueous-removable protective cover and allow the nasal sinus ostial implant to expand;
   v) hydrating the nasal ostial implant to swell the nasal ostial implant, and then removing the guide shaft without removing the nasal ostial implant, the first diameter expanding by at least 15% when water is absorbed therein as compared to the first diameter of the polymeric tube in a dry state;
   vi) the aqueous-swellable and biodegradable polymer remaining in the mammalian ostium for at least one hour after insertion into the mammalian ostium and after being swollen and kept moist by a moist aqueous environment within the mammalian ostium; and
   vii) allowing the nasal ostial implant to biodegrade.

12. The method of claim 11 wherein the nasal ostium implant has the aqueous-removable protective cover in contact with and over the outer surface of the cylindrical polymeric tube and hydrating the nasal ostium implant disrupts the aqueous removable cover.

13. The method of claim 12 wherein the aqueous removable cover has physical striations, serrations, or intentional deficiencies in its structure to facilitate disruption of the aqueous-removeable cover as a result of hydration of the aqueous-removeable cover.

14. The method of claim 11 wherein the protective cover comprises an aqueous soluble, aqueous dispersible, or aqueous degradable organic material.

15. The method of claim 11 wherein the nasal ostial implant is carried on a hand-held device and inserted by the hand-held-device into the ostium of a human being comprising, and the hand-held-device further comprises:
  a) a blunt needle; and
  b) a physical stop to locate the ostial implant placed on the hand-held device.

16. The method of claim 11 wherein the sinus ostial implant further comprises at least one of A) a surrounding shaft to stiffen the blunt needle as necessary; B) perforations, holes, slits, or other defects at select locations around the circumference of the needle to facilitate radial flow of one or more fluids or a mixture of one or more fluids and one or more of the solids into the nasal ostial implant when the needle is so supplied.

17. A method of maintaining an open sinus ostium in a mammal using a polymeric medical implant comprising an aqueous swellable and biodegradable polymer, the temporary medical implant being a nasal ostial implant comprising:
  g) an aqueous-removable protective cover;
  h) a cylindrical polymeric tube having a length, an outer surface with a first diameter, and a cross-section;
  i) the aqueous-removable protective cover in contact with and positioned over the outer surface of the cylindrical polymeric tube;
  j) the aqueous-removable protective cover maintaining the dimensions of the nasal ostial implant against forces of expansion, the aqueous-removable protective cover being biocompatible and disruptable by hydration;
wherein the nasal ostial implant is attached to a tool comprising; and
  k) a guide shaft having a distal end of the guide shaft and the guide shaft having a lumen; and
  l) the guide shaft supporting the nasal ostial implant extending from, adjacent to or along the distal end of the guide shaft; and
wherein the method comprises
  g) using the guide shaft to insert the nasal ostial implant into the mammalian ostium;
  m) inserting the guide shaft with the tip while the guide shaft is supporting the nasal ostial implant comprising the aqueous swellable and biodegradable polymer into the sinus ostium of the mammal;
  n) hydrating the aqueous-removable protective cover in contact with and positioned over the outer surface of the cylindrical polymeric tube to disrupt the aqueous-removable protective cover and allow the nasal ostial implant to expand;
  o) hydrating the implant to swell the nasal ostial implant, and then removing the guide shaft without removing the implant, the first diameter expanding by at least 15% when water is absorbed therein as compared to a first diameter of the polymeric tube in a dry state;
  p) the aqueous-swellable and biodegradable polymer remaining in the mammalian ostium for at least one hour after insertion into the mammalian ostium and after being swollen and kept moist by a moist aqueous environment within the mammalian ostium; and
  q) the nasal ostial implant biodegrading.

* * * * *